United States Patent
Warner et al.

(10) Patent No.: US 9,551,643 B2
(45) Date of Patent: Jan. 24, 2017

(54) FLOW CYTOMETRIC SYSTEMS FOR STERILE SEPARATION OF MAGNETICALLY LABELED SAMPLE COMPONENTS

(71) Applicant: BECTON, DICKINSON AND COMPANY, Franklin Lakes, NJ (US)

(72) Inventors: Brian David Warner, Martinez, CA (US); Liping Yu, San Jose, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 14/365,602

(22) PCT Filed: Nov. 26, 2012

(86) PCT No.: PCT/US2012/066555
§ 371 (c)(1),
(2) Date: Jun. 13, 2014

(87) PCT Pub. No.: WO2013/095867
PCT Pub. Date: Jun. 27, 2013

(65) Prior Publication Data
US 2015/0010939 A1 Jan. 8, 2015

(51) Int. Cl.
*A61J 1/10* (2006.01)
*B01L 3/00* (2006.01)
(Continued)

(52) U.S. Cl.
CPC ...... *G01N 15/0656* (2013.01); *G01N 35/0098* (2013.01); *G01N 2015/0065* (2013.01);
(Continued)

(58) Field of Classification Search
CPC ............... B01L 2200/0652; B01L 2300/0877; B01L 2400/043; B01L 2400/0439; B01L 3/502761; B03C 1/288; B03C 2201/18; G01N 15/02; G01N 15/1056; G01N 15/1459; G01N 2015/0288; G01N 2015/1006; G01N 33/54326; G01N 15/0656; G01N 2015/0065
(Continued)

(56) References Cited

U.S. PATENT DOCUMENTS 8,455,258 B2 * 6/2013 Quake .................... B01D 57/02
422/502
8,727,132 B2 * 5/2014 Miltenyi et al. .......... 210/360.1
(Continued)

FOREIGN PATENT DOCUMENTS

EP 0672458 A2 9/1995
JP 4-500008 A 1/1992
(Continued)

OTHER PUBLICATIONS

Jayasinghe et al, "Sterile and Disposable Fluidic Subsystem Suitable for Clinical High Speed Fluorescence-Activated Cell Sorting", Cytometry Part B (Clinical Cytometry) 70B:344-354 (2006).
(Continued)

*Primary Examiner* — Dean Kwak
(74) *Attorney, Agent, or Firm* — Bret E. Field; Bozicevic, Field & Francis LLP

(57) ABSTRACT

Systems for sterile separation of magnetically labeled sample components and methods for using the same are provided. Embodiments of the systems include a magnetic separation device and a pliant sample container, where a portion of the pliant sample container is operatively coupled under pressure to the magnetic separation device. Also provided are methods of using the systems, as well as pliant sample containers configured for use with the subject systems and methods.

9 Claims, 14 Drawing Sheets

(51) Int. Cl.
*G01N 15/06* (2006.01)
*G01N 35/00* (2006.01)
*G01N 15/00* (2006.01)
*G01N 15/10* (2006.01)
*G01N 15/14* (2006.01)

(52) U.S. Cl.
CPC ............ *G01N 2015/1006* (2013.01); *G01N 2015/149* (2013.01); *G01N 2015/1409* (2013.01)

(58) Field of Classification Search
USPC ............ 422/22, 73, 147, 186, 527, 533
See application file for complete search history.

(56) References Cited

U.S. PATENT DOCUMENTS

| | | | |
|---|---|---|---|
| 2004/0142463 A1* | 7/2004 | Walker et al. | 435/325 |
| 2005/0011582 A1* | 1/2005 | Haug | G01N 15/1404 141/65 |
| 2011/0020855 A1* | 1/2011 | Shinoda et al. | 435/29 |
| 2011/0137018 A1 | 6/2011 | Chang-Yen et al. | |
| 2012/0164718 A1* | 6/2012 | Bishop | G01N 15/00 435/288.7 |
| 2013/0330739 A1 | 12/2013 | Yu | |
| 2014/0120570 A1 | 5/2014 | Yu et al. | |

FOREIGN PATENT DOCUMENTS

| | | |
|---|---|---|
| JP | 2000-516345 A | 12/2000 |
| WO | 90/04019 A1 | 4/1990 |
| WO | 99/26067 A1 | 5/1999 |
| WO | 2010033140 A2 | 3/2010 |

OTHER PUBLICATIONS

Miltenyi Biotec GmbH, CliniMACS® Cell Separation Systems, Product Catalog 2008, 48 pages.
Miltenyi Biotec GmbH, CliniMACS® User Manual, US Edition, Software 2.40, Jan. 2014, 128 pages.
Miltenyi Biotec GmbH, CliniMACS® User Manual for the CliniMACS® CD34 Reagent System, Jan. 2014, 102 pages.
Sandin et al. "Magnetophoresis and cytometry with magnetic microparticles", International Congress Series, Jun. 2007, vol. 1300, pp. 271-274.
Yang et al. "Micro flow cytometry utilizing a magnetic bead-based immunoassay for rapid virus detection", Biosensors and Bioelectronics, Dec. 1, 2008, vol. 24, No. 4, pp. 855-862.
Extended EP Search Report issued Jul. 13, 2015 in related EP Application No. 12859016.3, 7 pages.

* cited by examiner

FLOW CYTOMETRIC SYSTEMS FOR STERILE SEPARATION OF MAGNETICALLY LABELED SAMPLE COMPONENTS

CROSS-REFERENCE TO RELATED APPLICATIONS

Pursuant to 35 U.S.C. §119 (e) this application claims priority to the filing date of U.S. Provisional Patent Application Ser. No. 61/578,785 filed Dec. 21, 2011; the disclosure of which application is herein incorporated by reference.

INTRODUCTION

Flow cytometry is a well-accepted tool in research that allows a user to rapidly analyze and sort components in a sample fluid. Flow cytometers use a carrier fluid (e.g., a sheath fluid) to pass the sample components, substantially one at a time, through a zone of illumination. Each sample component is illuminated by a light source, such as a laser, and light scattered by each sample component is detected and analyzed. The sample components can be separated based on their optical and other characteristics as they exit the zone of illumination.

Sterile flow cytometry in which the sample components of interest are separated under sterile conditions are becoming increasingly important. For example, flow cytometry is frequently used to sort and collect cells for experiments, such as in vivo transplantation and in vitro cell culture, in which it is desirable that the cells be free from interfering microorganisms. In particular, the fluid handling components of a flow cytometer directly contact the sample and sheath fluids and may be a source of contaminants from the surrounding environment.

Magnetic separation of cells flowing through a tube or cartridge positioned in an appropriately configured magnetic separation device has been shown to be very convenient. In magnetic separation devices, a sample fluid that includes magnetically labeled components flows through a tube positioned in a magnetic separation device, which includes a magnet. As the sample flows through the tube, magnetically labeled components in the sample are retained in the tube by the magnetic field produced by the magnet. Unlabeled components are not retained in the tube and flow through the magnetic separation device. The retained magnetically labeled components can be recovered by removing the magnetic field and flushing the magnetically labeled components from the tube.

SUMMARY

As reviewed above, magnetic separation of cells flowing through a tube or cartridge positioned in an appropriately configured magnetic separation device has been shown to be very convenient. The cartridges envisioned so far, however, do not easily lend themselves to sterile processing procedures. Additional pumping of a given sample through such a cartridge requires additional fluidic components, which complicates the procedure. When using the cartridge in conjunction with a cell sorter, high sample pressures are often required. However, high efficiency magnetic separations require the separation chamber to be positioned close to the magnetic pole pieces and the chamber walls to be as thin as possible. It is difficult to construct devices that simultaneously satisfy both requisite parameters.

Flow cytometric systems for sterile separation of magnetically labeled sample components and methods for using the same are provided. Systems described herein include a magnetic separation device and a pliant sample container configured to operatively couple to the magnetic separation device. In using systems of the invention, a pliant sample container as described herein that includes a magnetically labeled sample is operatively coupled under pressure to the magnetic separation device. For example, the pliant sample container may be present inside of a pressure chamber. Increasing the pressure of the pressure chamber forces sample from the pliant sample container through the operatively coupled magnetic separation device, thereby magnetically separating the sample components in a sterile manner. Where desired, the magnetically separated sample components may then be transferred to a flow cytometer, e.g., for sterile cell sorting applications.

Embodiments of the present disclosure include high efficiency, high flow rate and low cost magnetic separation of magnetically labeled components in a sample, while at the same time maintaining the sample in a sterile environment. As such, embodiments of the present disclosure may be used to separate cells or other molecules that are labeled with magnetic particles from a biological fluid sample in a sterile manner.

Systems of the present disclosure may be configured as a portion of a larger system. For example, systems of the present disclosure may be configured as a flow cytometric sample fluidic subsystem configured to deliver a sample fluid to a flow cytometer in a sterile manner. In certain embodiments, the flow cytometric sample fluidic subsystem includes a magnetic separation device and a pliant sample container, where a portion of the pliant sample container is operatively coupled under pressure to the magnetic separation device. For instance, the flow cytometric sample fluidic subsystem may be configured to maintain the portion of the pliant sample container operatively coupled to the magnetic separation device under pressure. In certain cases, the pliant sample container is present inside of a pressure chamber. In some instances, the magnetic separation device is configured to produce a magnetic field proximal to the portion of the pliant sample container operatively coupled to the magnetic separation device. In other embodiments, the flow cytometric sample fluidic subsystem includes a first pressure chamber housing a fluid reservoir of the pliant sample container and a second pressure chamber housing the portion of the pliant sample container operatively coupled to the magnetic separation device. The second pressure chamber may be coupled to the first pressure chamber. In certain instances, the magnetic separation device is configured to produce a magnetic field proximal to the portion of the pliant sample container operatively coupled to the magnetic separation device.

In certain embodiments, a fluid is contained in a pliant sample container. In certain instances, the fluid is sterile. The sample container may be sealed from the surrounding environment to maintain the sterility of the fluid. In some cases, the pliant sample container includes a fluid reservoir configured to contain a volume of the fluid and a conduit fluidically coupled to the fluid reservoir and configured to direct a flow of the fluid through the magnetic separation device. The sample container may also include an alignment guide attached to the conduit and configured to operatively couple the conduit with the magnetic separation device. To facilitate alignment of the conduit in the magnetic separation device, the magnetic separation device may include a corresponding alignment guide (such as, but not limited to, a notch) configured to mate with and position the portion of the pliant sample container in the magnetic separation device. For example, the corresponding alignment guide (e.g., notch) may be configured to mate with the alignment guide attached to the conduit and position the conduit in the magnetic separation device. In certain instances, when the conduit is aligned in the magnetic separation device, a longitudinal axis of the conduit is substantially parallel to a longitudinal axis of the magnetic separation device.

Additional aspects of the pliant sample container include that the fluid reservoir may include one or more ports. In addition, certain embodiments of the pliant sample container include a fluid reservoir where the walls of the fluid reservoir have a thickness of 0.2 mm or less. In certain instances, the conduit of the pliant sample container is removably coupled to the fluid reservoir. In some cases, the conduit has walls with a thickness of 0.5 mm or less.

In certain embodiments, the magnetic separation device includes a first wedge-shaped magnetic field guide disposed on a surface of a first magnetic field source and a second wedge-shaped magnetic field guide disposed on a surface of a second magnetic field source. The first wedge-shaped magnetic field guide may have a first apex edge and the second wedge-shaped magnetic field guide may have a second apex edge. In some cases, the first apex edge is aligned substantially across from and parallel to the second apex edge. For instance, the first apex edge may be a substantially uniform distance along its length from the second apex edge. Positioning the conduit between and substantially parallel to the apex edges of the magnetic field guides may maximize the amount of time the sample fluid flow is exposed to the locally high magnetic field and magnetic field gradient in the area between the apex edges of the magnetic field guides, and thus may increase the separation efficiency of the device.

During use, a conduit of a pliant sample container is operatively coupled to a magnetic separation device. As described above, pliant sample container may include a fluid reservoir fluidically coupled to the conduit and configured to contain a volume of a fluid, where the conduit is configured to direct a flow of the fluid through the magnetic separation device, and an alignment guide attached to the conduit and configured to operatively couple the conduit with the magnetic separation device. In certain embodiments, the pliant sample container is present inside of a pressure chamber. In some cases, the magnetic separation device is configured to produce a magnetic field proximal to the conduit. In other embodiments, a fluid reservoir of the pliant sample container is present inside of a first pressure chamber and the conduit is present inside of a second pressure chamber. In certain instances, the second pressure chamber is coupled to the first pressure chamber. In some cases, the magnetic separation device is configured to produce a magnetic field proximal to the conduit. The pressure chamber is sealed and pressure is applied to the fluid reservoir to transport the sample fluid from the fluid reservoir through the conduit positioned in the magnetic separation device. For example, the pressure chamber may be pressurized with a gas. In some cases, the increase in pressure in the pressure chamber acts on the fluid reservoir, forcing the fluid out of the fluid reservoir and through the conduit positioned in the magnetic separation device. In certain instances, because the fluid reservoir is sealed from the surrounding environment, the system maintains the sterility of the sample fluid. For instance, the sample fluid is not exposed to the surrounding gas used to pressurize the pressure chamber, or to fluidic components typically used to transport a sample fluid (e.g., a pump).

Prior to applying pressure on the fluid reservoir to transport the sample fluid from the fluid reservoir through the conduit, a sample may be added to the fluid reservoir. In certain cases, the sample includes a target component of interest. In some instances, the sample is a biological sample. Methods of the present disclosure further include magnetically labeling the target component of interest. For example, the method may include specifically attaching a magnetic label to the target component to produce a magnetically labeled component prior to applying pressure to the fluid reservoir.

After applying pressure to the fluid reservoir, as the sample fluid flows through the conduit, magnetically labeled components in the sample are retained in the conduit by a magnetic field produced by the magnetic separation device. Non-labeled components in the sample are not retained in the conduit and flow through the magnetic separation device. The retained magnetically labeled components can be recovered by positioning the conduit away from the magnetic field and washing the magnetically labeled components from the conduit.

In some cases, the pliant sample container also includes a fluid transfer tube fluidically coupled to the conduit. For example, the fluid transfer tube may be in fluid communication with and positioned downstream from the conduit. The fluid transfer tube may be configured to transport the sample fluid outside the pressure chamber. In certain instances, the fluid transfer tube is removably coupled to the conduit. The fluid transfer tube may include at least a portion of a check valve, where the check valve is configured to regulate the pressure inside the pressure chamber. In certain instances, the system also includes one or more additional devices positioned downstream from the pliant sample container. Further analysis and/or processing of the magnetically labeled components in the sample fluid may be performed by the additional devices, which may include, for example, a concentration device (e.g., an acoustic concentration device) and a flow cytometer.

DETAILED DESCRIPTION

Figure 1:
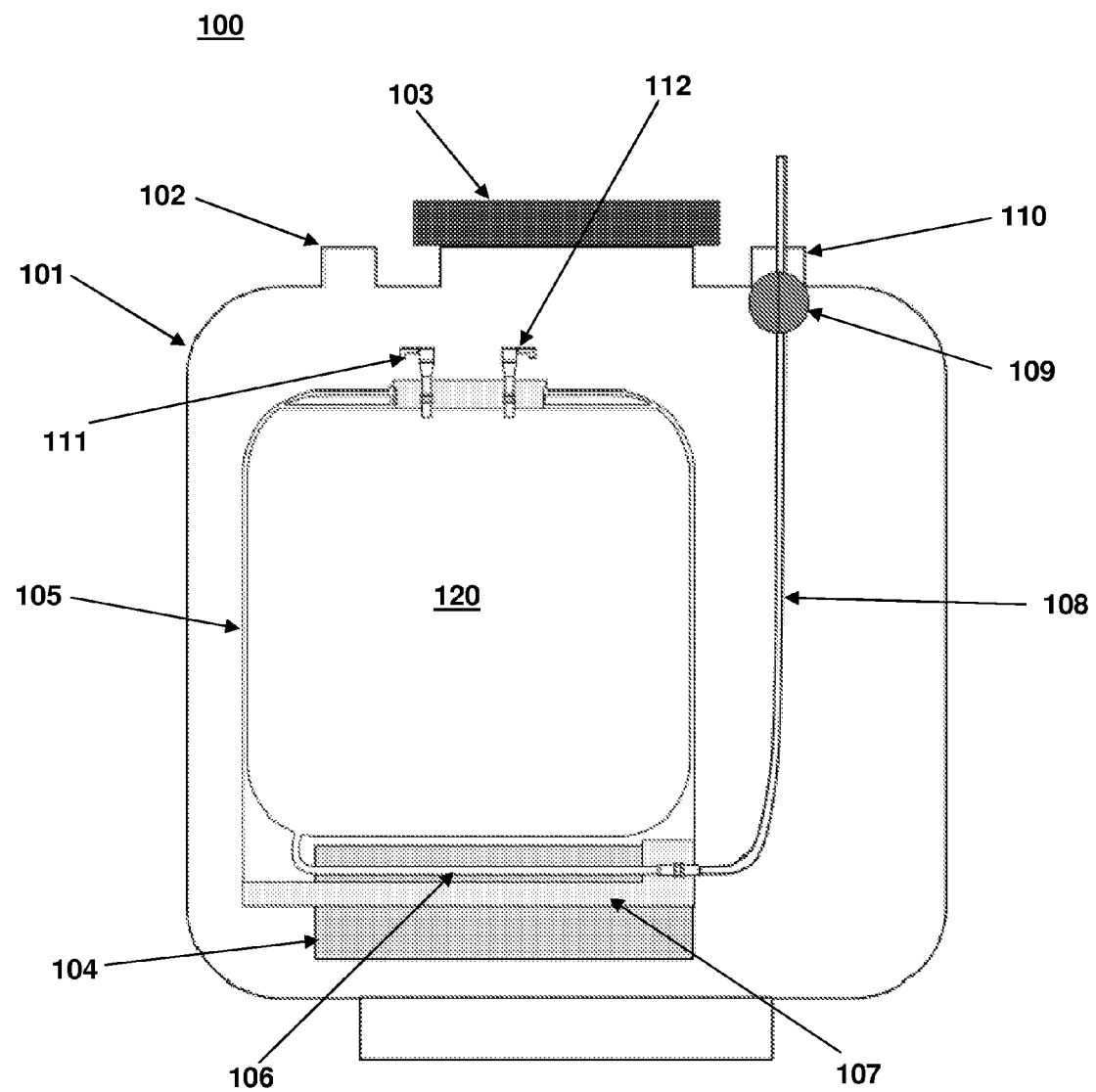
FIG. 1 shows a schematic of a system that includes a pressure chamber and a magnetic separation device inside of the pressure chamber, according to embodiments of the present disclosure.

As summarized above, flow cytometric systems for sterile separation of magnetically labeled sample components and methods for using the same are provided. Systems described herein include a pressure chamber having a magnetic separation device and a pliant sample container configured to operatively couple to the magnetic separation device. In using systems of the invention, a pliant sample container, as described herein, that includes a magnetically labeled sample is operatively coupled to the magnetic separation device of the pressure chamber and sealed in the pressure chamber. Increasing the pressure in the pressure chamber moves sample from the pliant sample container through the operatively coupled magnetic separation device, thereby magnetically separating the sample components in a sterile manner. Where desired, the magnetically separated sample components may then be transferred to a flow cytometer, e.g., for sterile cell sorting applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments of the present disclosure, aspects of embodiments of the flow cytometric sample fluidic subsystems will be described first in greater detail. Next, embodiments of the flow cytometric fluidic pressure chamber, pliant sample container, magnetic separation devices, methods and kits that may be used with the flow cytometric sample fluidic subsystems are reviewed.

Flow Cytometric Fluidic Subsystems

Provided are flow cytometric sample fluidic subsystems for separating magnetically labeled components in a sample. The subsystems may be configured to separate magnetically labeled components from non-magnetically labeled components (e.g., components that are not associated with a magnetic label) in the sample. In certain embodiments, the subsystems are configured to separate magnetically labeled components in a sample while at the same time maintaining the sample in a substantially sterile environment. By "sterile" is meant a sample that is free or substantially free from live bacteria or other microorganisms. In some cases, maintaining a sample in a sterile environment may facilitate subsequent processing or use of the components in the sample, for example in in vitro cell cultures, in vivo animal transplantations, collection of cellular proteins, and the like.

In certain instances, the subsystem separates magnetically labeled components of interest from components that are not of interest (e.g., components that are not magnetically labeled) by retaining the magnetically labeled components in the subsystem while not retaining components that are not of interest. Because the components of interest are magnetically labeled, the subsystem may be configured to retain the magnetically labeled components in the subsystem by attracting the magnetically labeled components to a magnetic field source in the subsystem and retaining the magnetically labeled components in the subsystem. In some cases, the subsystem separates magnetically labeled components that are not of interest from components that are of interest (e.g., components of interest that are not magnetically labeled) by retaining the magnetically labeled components that are not of interest in the subsystem while not retaining components that are of interest. In these embodiments, because the components of interest are not magnetically labeled, the components of interest are not retained in the subsystem and flow through the subsystem. The subsystem may be configured to retain the magnetically labeled components that are not of interest in the subsystem by attracting the magnetically labeled components to a magnetic field source in the subsystem and retaining the magnetically labeled components that are not of interest in the subsystem.

The subsystem may be configured to provide a flow of a fluid through a magnetic separation device to separate magnetically labeled components of interest from a sample fluid. In some instances, the subsystem is configured to provide a flow of a fluid from the magnetic separation device in the flow cytometric sample fluidic subsystem to a subsequent concentration and/or analysis device. In certain embodiments, the subsystem is configured to have a flow rate of 1 µL/min or more, such as 10 µL/min or more, including 50 µL/min or more, or 100 µL/min or more, or 200 µL/min or more, or 300 µL/min or more, or 400 µL/min or more, or 500 µL/min or more, or 750 µL/min or more, or 1 mL/min or more, or 2 mL/min or more, or 5 mL/min or more, or 10 mL/min or more.

The subsystem may be configured to separate magnetically labeled components from a simple sample or complex sample. By "simple sample" is meant a sample that includes one or more magnetically labeled components and few, if any, other molecular species apart from the solvent. By "complex sample" is meant a sample that includes the one or more magnetically labeled components of interest and also includes many different proteins and other molecules that are not of interest. In certain embodiments, the complex sample is a blood sample, by which is meant whole blood or a fraction thereof, e.g., serum or plasma. In certain embodiments, the complex sample is a serum sample. In certain embodiments, the complex sample separated using the subsystems disclosed herein is one that includes 10 or more, such as 20 or more, including 100 or more, e.g., $10^3$ or more, $10^4$ or more (such as 15,000, 20,000 or even 25,000 or more) distinct (i.e., different) molecular entities that differ from each other in terms of molecular structure.

In certain embodiments, the subsystem is configured to separate magnetically labeled components from a biological sample. A "biological sample" encompasses a variety of sample types obtained from an organism and can be used in a diagnostic or monitoring assay. The definition encompasses blood, blood-derived samples, and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, enrichment for certain components, or labeling (e.g., labeling with a magnetic label). The term "biological sample" encompasses a clinical sample, and also includes cells in culture, cell supernatants, cell lysates, serum, plasma, cerebrospinal fluid, urine, saliva, biological fluid, and tissue samples.

Components of interest may include any component that can be stably associated with a magnetic label detectable by the subsystems disclosed herein. By "stably associated" is meant that the magnetic label and the component of interest maintain their position relative to each other in space under the conditions of use, e.g., under the assay conditions. As such, the magnetic label and the component of interest can be non-covalently or covalently stably associated with each other. Examples of non-covalent associations include non-specific adsorption, binding based on electrostatic (e.g. ion, ion pair interactions), hydrophobic interactions, hydrogen bonding interactions, specific binding through a specific binding pair member covalently attached to the component of interest or the magnetic label, combinations thereof, and the like. Examples of covalent binding include covalent bonds formed between the magnetic label and a functional group present on the component of interest, e.g. —OH, where the functional group may be naturally occurring or present as a member of an introduced linking group. Accordingly, the magnetic label may be adsorbed, physisorbed, chemisorbed, or covalently attached to the surface of the component of interest.

Flow cytometric sample fluidic subsystems according to embodiments of the present disclosure include a magnetic separation device and a pliant sample container, where a portion of the pliant sample container is operatively coupled under pressure to the magnetic separation device. In certain instances, the pliant sample container is present inside of a pressure chamber. Embodiments of the pressure chamber and the magnetic separation device are discussed in greater detail below.

Pressure Chamber

As described above, embodiments of the subsystem include a pressure chamber. The pressure chamber includes a sealable opening and an inlet configured to receive a pressurized gas. In certain embodiments, the pressure chamber is configured to maintain an elevated pressure within the pressure chamber. For example, the pressure chamber may be configured to maintain a pressure greater than standard atmospheric pressure within the pressure chamber. In some instances, the pressure chamber is configured to maintain a pressure within the pressure chamber of 25 psi or more, such as 50 psi or more, or 75 psi or more, including 100 psi or more, or 125 psi or more, for example 150 psi or more. In some cases, the pressure chamber is made of a material capable of retaining the elevated pressures within the pressure chamber. For example, the pressure chamber may be made of a material capable of retaining the elevated pressures within the pressure chamber without any significant structural changes, such as cracking, deformation from its original shape, etc. In some instances, the pressure chamber is made of a metal, such as stainless steel.

In certain embodiments, the pressure chamber includes an opening to facilitate access into the interior of the pressure chamber. The opening may be a sealable opening. In some instances, the sealable opening is configured to have an airtight seal. The sealable opening may facilitate maintaining an elevated pressure within the pressure chamber as described above. In some cases, the sealable opening includes a sealable cover. The sealable cover may be attached to the pressure chamber so as to maintain an airtight seal with the pressure chamber. For example, the sealable cover may be attached to the pressure chamber by a screw thread engagement, a clamp, combinations thereof, and the like. The cover may be made of the same material as the pressure chamber, such as a metal (e.g., stainless steel, and the like). In certain instances, the cover includes one or more sections made of a transparent or translucent material, such as, but not limited to glass, plastic, and the like. The sealable opening may also include a gasket that fits between the cover and the pressure chamber. The gasket may extend around the periphery of the opening in the pressure chamber and may facilitate maintaining an airtight seal between the interfacing surfaces the cover and the pressure chamber.

In some instances, the opening in the pressure chamber is sized to allow a user to access the interior of the pressure chamber. The opening may be sized to allow a user to insert one or more hands into the interior of the pressure chamber. In some cases, the opening is sized to allow items, such as a pliant sample container as described herein, to be inserted and removed from the interior of the pressure chamber. For example, the opening may be circular and have a diameter of 10 cm or more, such as 15 cm or more, or 20 cm or more. The pressure chamber may have an interior volume sufficient to contain pliant sample containers of various sizes. For example, the pressure chamber may have an interior volume of 1 L or more, such as 5 L or more, including 10 L or more, or 15 L or more, for instance 20 L or more, or 25 L or more, etc.

Embodiments of the pressure chamber further include an inlet configured to receive a pressurized gas from a gas source. The pressurized gas may be any convenient type of gas suitable for pressurizing the pressure chamber. For instance, the pressurized gas may include air, nitrogen, argon, and the like. The pressurized gas may be of a composition ideally suited for preservation of the sample during use. In some embodiments, the pliant sample container can be constructed of a material configured to allow partial pressures of a dissolved gas in the sample fluid to be maintained at levels suitable for survival of cells and/or other biological material in the sample. In some cases, the gas source is a source of a pressurized gas, such as, but not limited to, a pressurized gas cylinder, a compressor, and the like. In certain instances, the pressurized gas has a pressure of 25 psi or more, such as 50 psi or more, or 75 psi or more, including 100 psi or more, or 125 psi or more, for example 150 psi or more. The pressure chamber may also include an outlet configured to release the pressurized gas from the pressure chamber.

In certain embodiments, the pressure chamber includes a valve configured to regulate the pressure inside the pressure chamber. In some cases, the valve is an adjustable valve. The adjustable valve may be configured to be adjustable to various different positions, such as fully open, fully closed, or any one of a number of different positions between fully open and fully closed. In certain instances, the valve is in fluid communication with the inlet and is configured to regulate the pressure in the pressure chamber by adjusting the amount of pressurized gas entering into the pressure chamber. In some cases, the valve is in fluid communication with the outlet and is configured to regulate the pressure in the pressure chamber by adjusting the amount of gas leaving the pressure chamber. For example, the valve may be a check valve, such as a ball check valve. In certain embodiments the check valve is configured to close the outlet of the pressure chamber, such that the pressure in the pressure chamber may be increased by inputting a pressurized gas through the inlet of the pressure chamber. To release the pressure in the pressure chamber, the check valve may be configured to open the outlet to allow pressurized gas in the pressure chamber to exit into the surrounding environment.

The pressure chamber may further include additional elements associated with the operation and use of the pressure chamber. For example, the pressure chamber may include a pressure detector. The pressure detector may be configured to determine the pressure inside the pressure chamber and display an indication of the pressure inside the pressure chamber to a user. The pressure chamber may further include one or more inlets and/or outlets in addition to the inlet and outlet described above. For instance, the pressure chamber may include a second gas inlet and/or a second gas outlet. In some cases, the pressure chamber includes one or more fluid inlets configured to carry a fluid, such as a sample fluid, reagent, etc., into the pressure chamber. In certain instances, the pressure chamber includes one or more fluid outlets configured to carry a fluid, such as a sample fluid, waste stream, etc., out of the pressure chamber.

In certain embodiments, the pressure chamber includes an agitation device. The agitation device may be configured to agitate the pliant sample container. Agitation of the pliant sample container may facilitate agitation of the sample fluid in the pliant sample container to keep sample components, such as cells, suspended during the separation process. The agitation device may be any convenient agitation device, such as but not limited to, a shaker, a stirrer, and the like.

Magnetic Separation Device

As reviewed above, the pressure chamber includes a magnetic separation device. The magnetic separation device is present inside of the pressure chamber and configured to operatively couple to a pliant sample container. In some instances, the magnetic separation device is configured to separate magnetically labeled components in a sample fluid as the sample fluid flows through the magnetic separation device. The magnetic separation device may be positioned in the pressure chamber in a horizontal orientation, such that the flow of the sample fluid through the magnetic separation device is substantially horizontal. In other embodiments, the magnetic separation device is positioned in the pressure chamber in a vertical orientation, such that the flow of the sample fluid through the magnetic separation device is substantially vertical. In yet other embodiments, the magnetic separation device is positioned in the pressure chamber at any convenient angle with respect to the bottom of the pressure chamber.

The magnetic separation devices may be configured to separate magnetically labeled components in a sample fluid as the sample fluid flows through the magnetic separation device. The magnetic separation device may be configured to produce a magnetic field. In some instances, the device is configured to produce a magnetic field sufficient to separate the magnetically labeled components in the sample. In some cases, the magnetic field device is configured to produce a magnetic field having a magnetic force sufficient to separate magnetically labeled components form non-magnetically labeled components in the sample.

The magnetic separation device may be any of a variety of magnetic separation devices. For example, the magnetic separation device may include embodiments described in detail in U.S. Pat. Nos. 7,927,561, 6,672,458, 6,433,160, 5,973,138, and 5,945,281, the disclosures of each of which are incorporated herein by reference in their entirety.

In certain embodiments, the magnetic separation device may include one or more magnetic field sources. In addition, in some cases, the magnetic separation device includes one or more magnetic field guides configured to direct the magnetic field from the magnetic field source to the sample flow path.

In certain embodiments, the magnetic separation device includes two magnetic field sources, although the device may include any number of magnetic field sources, such as 2, 3, 4, 5, 6, 7, 8, 9, 10 or more magnetic field sources as desired. For instance, the device may include a first magnetic field source and a second magnetic field source. In certain embodiments, the first and second magnetic field sources are arranged such that a magnetic field is produced in an area between the magnetic field sources. As such, the first and second magnetic field sources may be configured to produce a magnetic field sufficient to retain the magnetically labeled components in an area between the magnetic field sources.

The magnetic field source may include permanent magnets, electromagnets, superconducting magnets, combinations thereof, and the like. In certain embodiments, the magnetic field source includes one or more permanent magnets. By "permanent magnet" is meant a magnetic material has a persistent magnetic field such that the magnetic field does not substantially decrease over time. In contrast, the term "soft magnet" refers to a material that can be magnetized in the presence of an applied external magnetic field, but whose magnetism substantially decreases when the external magnetic field is removed. In embodiments where the magnetic field source includes one or more permanent magnets, the use of permanent magnets may facilitate the production of a magnetic field without the need for external energy input into the device to power a magnetic field source. In certain cases, when the magnetic field source includes one or more permanent magnets, the use of permanent magnets may facilitate the production of a device that is less complex than a device that includes electromagnets and/or superconducting magnets. For example, embodiments of devices that include permanent magnets may not need to include components associated with electromagnets and/or superconducting magnets, such as a power source, electrical circuits associated with the magnetic field source, cooling components associated with electromagnets and/or superconducting magnets, temperature sensors, and the like.

In certain embodiments, the magnetic field source includes a permanent magnet, such as a rare-earth magnet. Rare-earth magnets include, but are not limited to, samarium-cobalt magnets (e.g., $SmCo_5$), neodymium alloy (NdFeB) magnets (e.g, $Nd_2Fe_{14}B$), and the like.

Aspects of the magnetic separation device also include one or more magnetic field guides. The magnetic field guide may be configured to direct the magnetic field from the magnetic field source to the sample flow path. In certain instances, the magnetic field guide is configured to focus the magnetic field produced by the magnetic field source. The magnetic field guide may focus the magnetic field by increasing the magnetic flux of the magnetic field, where the magnetic flux is the amount of magnetic field (e.g., the magnetic field density) that passes through a given surface area.

In certain embodiments, the magnetic field guide is configured to focus the magnetic field by having a tapered shape and by directing the magnetic field from the magnetic field source through the tapered shape of the magnetic field guide. By "tapered" is meant that the magnetic field guide has a wider end with a larger cross-sectional area and the cross-sectional area of the magnetic field guide becomes progressively smaller towards a narrower opposing end of the magnetic field guide. For example, the magnetic field guide may have a wedge-shape, where the base of the wedge has an area. Cross-sections of the wedge taken parallel to the base of the wedge will have progressively smaller areas towards the end of the wedge opposite from the base (i.e., towards the apex edge of the wedge). The term "wedge-shaped" as used herein is meant to include embodiments of the magnetic field guide that have an apex edge with a cross-sectional profile that tapers to a point at the apex edge. The term "wedge-shaped" also includes embodiments of the magnetic field guide that have an apex edge with a cross-sectional profile that does not taper to a point at the apex edge. For example, the apex edge of the magnetic field guide may have a cross-sectional profile that is rounded, truncated, blunted, and the like.

In some instances, the magnetic field guide has a wedge-shape and is configured to direct the magnetic field from the base of the wedge, which is disposed on a surface of the magnetic field source, to the apex edge of the wedge. Directing the magnetic field from the base of the wedge to the apex edge of the wedge may facilitate an increase in the magnetic flux of the magnetic field from the magnetic field source, as described above. An increase in the magnetic flux at the apex edge of the wedge-shaped magnetic field guide may produce a higher magnetic field and a higher magnetic field gradient proximal to the apex edge of the magnetic field guide than would be present in the absence of the magnetic field guide. Other tapered shapes for the magnetic field guides are possible, such as, but not limited to, pyramid, cone, frustum, combinations thereof, and the like.

In some instances, a first magnetic field guide is associated with the first magnetic field source, and a second magnetic field guide is associated with the second magnetic field source. In certain cases, the first magnetic field guide is positioned on the first magnetic field source and the second magnetic field guide is positioned on the second magnetic field source on the surface of the second magnetic field source such that the apex edge of the first magnetic field guide is proximal to the apex edge of the second magnetic field guide. In some cases, the apex edge of the first magnetic field guide is substantially parallel to the apex edge of the second magnetic field guide. The apex edge of the first magnetic field guide may be aligned across from the apex edge of the second magnetic field guide. For example, the apex edge of the first magnetic field guide may be aligned substantially directly across from the apex edge of the second magnetic field guide.

In certain embodiments, the magnetic field guide includes a soft magnet. The term "soft magnet" refers to a material that can be magnetized in the presence of an applied external magnetic field, but whose magnetism substantially decreases when the external magnetic field is removed. Soft magnets may include, but are not limited to, ferromagnetic materials, such as iron (e.g., annealed iron), stainless steel and nickel, ferrimagnetic materials, such as ceramic oxides of metals, combinations thereof, and the like.

As reviewed above, certain embodiments of the magnetic separation devices include a first wedge-shaped magnetic field guide disposed on a surface of a first magnetic field source, and a second wedge-shaped magnetic field guide disposed on a surface of a second magnetic field source. In certain embodiments, the first wedge-shaped magnetic field guide has a first apex edge, the second wedge-shaped magnetic field guide has a second apex edge, and the first apex edge is aligned substantially across from and parallel to the second apex edge. The first apex edge may be positioned at a substantially uniform distance along its length from the second apex edge.

The magnetic field guides are wedge-shaped and may be configured to direct the magnetic flux from the associated magnetic field sources towards the area between the apex edges of the magnetic field guides. In some cases, the wedge-shaped magnetic field guides focus the magnetic flux from the interface between each magnetic field source and the corresponding magnetic field guide, where the interface has a relatively large cross-sectional area, to the apex edge of each magnetic field guide, which has a relatively small cross-sectional area. The wedge-shaped magnetic field guides may be configured to focus the magnetic flux from the associated magnetic field sources with minimal magnetic flux leakage during the transmission of the magnetic flux through the magnetic field guides. In certain embodiments, the tapered wedge shape of the magnetic field guides focus the magnetic flux from the associated magnetic field sources, resulting in an increase in the magnetic flux from the magnetic field sources in the area between the apex edges of the magnetic field guides. The resulting high magnetic field strength and high magnetic field gradient in the area between the apex edges of the magnetic field guides may increase the efficiency of the separation of magnetically labeled components from non-labeled components in the sample being analyzed.

Figure 2A:
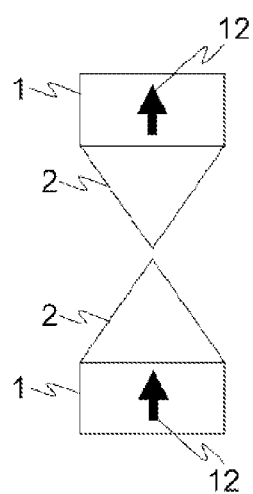
FIG. 2(a) shows a schematic of a front view of a magnetic separation device, according to embodiments of the present disclosure.
Figure 2B:
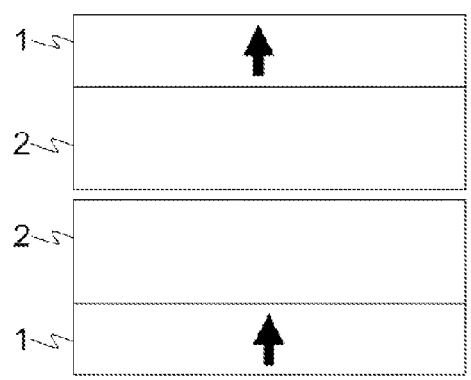
FIG. 2(b) shows a schematic of a side view of a magnetic separation device, according to embodiments of the present disclosure.
Figure 2C:
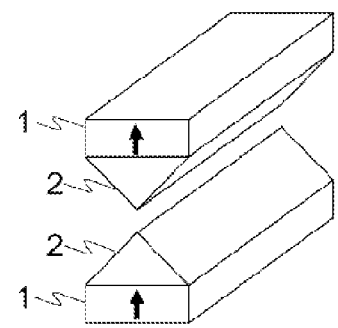
FIG. 2(c) shows a schematic of a three-dimensional perspective view of a magnetic separation device, according to embodiments of the present disclosure.

An example of an embodiment of a magnetic separation device according to the present disclosure is shown in the schematic illustrations in FIGS. 2(a), 2(b) and 2(c). The device includes two soft magnetic field guides 2. Each magnetic field guide 2 is attached to a permanent magnet 1. The two soft magnetic field guides 2 have a tapered shape from the end attached to the permanent magnet 1 towards the apex edges of the two magnetic field guides that are directly opposite each other. The apex edges of the magnetic field guides 2 are substantially linear, as shown in FIGS. 2(b) and 2(c). The permanent magnet 1 has magnetizations 12 that are in the same direction and perpendicular to the interface between the permanent magnets 1 and the soft magnetic field guides 2. The magnetic field guides 2 and permanent magnets 1 form a permanent magnet driven magnetic flux concentration structure, where the magnetic flux from permanent magnets 1 is focused (e.g., increased) by the tapered shape of the magnetic field guides 2. The magnetic field guides 2 produce a locally high magnetic flux density in the area between the apex edges of the magnetic field guides. In certain instances, the high magnetic flux produces a high magnetic field and magnetic field gradient in the area between the apex edges of the magnetic field guides.

As described above, the magnetic separation devices may be configured to separate magnetically labeled components in a sample fluid. Any convenient magnetic label may be employed. Magnetic labels are labeling components that are retained by the device for separating magnetically labeled components in a sample. Magnetic labels of interest may be retained by the device if they flow through a portion of a conduit in close proximity to the magnetic field produced by the device, e.g., between the magnetic field sources and/or between the magnetic field guides of the device).

Magnetic labels useful in the practice of certain embodiments of the present disclosure are magnetic particles, such as, but not limited to ferromagnetic, paramagnetic, superparamagnetic, anti-ferromagnetic, or ferrimagnetic particles. In certain instances, the magnetic particles appear "nonmagnetic" (e.g., have a remnant magnetization of substantially zero) in the absence of a magnetic field. Magnetic particles with a substantially zero remnant magnetization may not substantially agglomerate with each other in solution in the absence of an external magnetic field.

The magnetic particles may be chemically stable in a biological environment, which may facilitate their use in the assay conditions. In some cases, the magnetic particles are biocompatible, i.e., water soluble and functionalized so that they may be readily attached to biomolecules of interest, e.g., an antibody that specifically binds to a target analyte. By associating or binding magnetic particles to a specific antibody, the magnetic particles may be targeted to a specific analyte through the specific binding interactions between the antibody and complementary antigen. In some instances, the magnetic label may be bound to the protein or antibody as described above through a non-covalent or a covalent bond with each other. Examples of non-covalent associations include non-specific adsorption, binding based on electrostatic (e.g. ion, ion pair interactions), hydrophobic interactions, hydrogen bonding interactions, specific binding through a specific binding pair member covalently attached to the surface of the magnetic particle, and the like. Examples of covalent binding include covalent bonds formed between the biomolecule and a functional group present on the surface of the magnetic particle, e.g. —OH, where the functional group may be naturally occurring or present as a member of an introduced linking group.

In certain embodiments, the magnetic particles are sized such that the magnetic particles are configured to be readily attached to a biomolecule of interest. In some cases, the magnetic particles are of a sufficiently small enough size such that the magnetic particles do not substantially interfere with the function of the biomolecule when the magnetic particles are attached to the biomolecule. For example, the magnetic particles may be of a sufficiently small size such that binding interactions of the attached biomolecule are not substantially hindered. In some cases, the magnetic particles are microparticles, and in some cases the magnetic particles are nanoparticles. In certain embodiments, the magnetic particles are substantially uniform in shape. For example, the magnetic particles may be spherical in shape. In addition to a spherical shape, magnetic nanoparticles suitable for use herein can be shaped as disks, rods, coils, fibers, pyramids, and the like.

Additional aspects of the magnetic separation devices are described in U.S. Provisional Application No. 61/479,778, filed on Apr. 27, 2011, the disclosure of which is incorporated herein by reference in its entirety.

In certain embodiments, the subsystem includes one or more magnetic separation devices for separating magnetically labeled components in a sample. Each of the one or more magnetic separation devices may be configured as described according to the present disclosure. For instance, the subsystem may include 2 or more magnetic separation devices, such as 3 or more, or 4 or more, or 5 or more, or 6 or more, or 7 or more, or 8 or more, or 9 or more, or 10 or more magnetic separation devices. The magnetic separation devices may be arranged in series such that the magnetic separation devices are fluidically coupled to each other one after another in a row. Arranging the magnetic separation devices in series may facilitate the progressive separation of magnetically labeled components from the same sample. In some instances, the magnetic separation devices are arranged in parallel. Arranging the magnetic separation devices in parallel may facilitate the simultaneous separation of magnetically labeled components from a plurality of samples. In certain cases, the magnetic separation devices are arranged in series and in parallel.

An example of an embodiment of a subsystem according to the present disclosure is shown in the schematic illustration in FIG. 1. The subsystem 100 includes a pressure chamber 101 and a magnetic separation device 104 positioned in the pressure chamber 101. The pressure chamber 101 includes a sealable opening and a cover 103 configured to form a substantially airtight seal on the pressure chamber 101. The pressure chamber 101 further includes a gas inlet 102 and an outlet 110. The outlet 110 is configured as a ball check valve. Ball 109 is shown positioned in outlet 110 to illustrate the ball check valve in a closed position.

Pliant Sample Container

Aspects of the present disclosure include a pliant sample container configured to operatively couple to a magnetic separation unit of the fluidic subsystems, e.g., as described above. By pliant is meant that the sample container may be bent or flexed from its original shape without any significant structural changes, such as tearing, cracking, perforating, etc. For example, a pliant sample container may be flexed and/or deformed from its original shape, while still maintaining a sealed barrier preventing contact between a fluid inside the sample container and the surrounding environment. In certain embodiments, the pliant sample container includes a fluid reservoir configured to contain a volume of a fluid, a conduit fluidically coupled to the fluid reservoir and configured to direct a flow of the fluid through a magnetic separation device, and an alignment guide configured to operatively couple the conduit with the magnetic separation device.

In some cases, the pliant sample container is made from a flexible material that has a Young's modulus of 1 GPa or less, such as 0.7 GPa or less, including 0.5 GPa or less, for instance, 0.3 GPa or less, or 0.1 GPa or less, such as 0.05 GPa or less, or 0.01 GPa or less.

In certain embodiments, the fluid in the pliant sample container is sterile. The pliant sample container may be configured to allow for the processing of a fluid (e.g., a sample fluid) through the magnetic separation device, while at the same time maintaining the sterility of the fluid. The pliant sample container may be configured as a single integrated unit that includes the fluid reservoir and the conduit, where the conduit is in fluid communication with and positioned downstream from the fluid reservoir. To facilitate maintaining the sterility of the fluid, the pliant sample container may be sealed from the surrounding environment. As described in more detail below, one or more inlets/outlets may be provided on the fluid reservoir and/or conduit, but the inlets/outlets may remain sealed until use.

Fluid Reservoir

Embodiments of the pliant sample container include a fluid reservoir. The fluid reservoir is configured to contain a fluid, which in some instances may be a sample fluid. In certain embodiments, the fluid is sterile. The fluid reservoir may be sealed to maintain the sterility of the fluid. For example, the fluid reservoir may be closed to the surrounding environment to prevent undesired contact between the fluid and the surrounding environment. Although the fluid reservoir may be sealed from the surrounding environment, the fluid reservoir may include one or more ports, such as one or more inlets and/or outlets. The one or more ports may be configured to permit access to the interior of the fluid reservoir when desired. For example, the fluid reservoir may include an inlet configured to allow a fluid, such as a sample fluid, reagent, etc. to be added to the fluid reservoir. In some cases, the fluid reservoir includes an outlet configured to allow fluid from the fluid reservoir to be removed from the fluid reservoir. The ports may be self-sealing ports, such that fluid can be added or removed from the fluid reservoir, for example using a syringe, and then the port seals itself to prevent contact between the fluid in the fluid reservoir and the surrounding environment.

In some instances, the fluid reservoir includes a fluid outlet. The fluid outlet may be configured to carry the fluid as the fluid flows out of the fluid reservoir. The fluid outlet may be in fluid communication with a conduit configured to direct a flow of the fluid through the magnetic separation device. In some cases, the fluid reservoir is directly connected to the conduit. In other embodiments, the fluid reservoir is connected to the conduit through a piece of tubing. For example, a proximal end of an extension tube may be connected to the fluid reservoir at the fluid outlet of the fluid reservoir. A distal end of the extension tube may be connected to the conduit. Fluid flowing out of the fluid reservoir through the fluid outlet may flow through the extension tube to the conduit. In some cases, the fluid reservoir further includes a clamp. The clamp may be configured to block the flow of fluid from the fluid reservoir. For instance, the clamp may be positioned around the extension tube. When configured in a closed position, the clamp substantially blocks the extension tube, for example by pinching the extension tube to occlude the inner lumen of the extension tube, and thus preventing fluid from flowing through the extension tube. When configured in an open position, the clamp does not block the flow of fluid through the extension tube.

In certain embodiments, the fluid reservoir is made from a flexible material. The fluid reservoir may be flexed and/or deformed from its original shape, while still maintaining the sterility of the sample fluid in the fluid reservoir. For instance, the fluid reservoir may be flexed and/or deformed from its original shape, while still maintaining a seal against contact between the sample fluid and the surrounding environment as described above. In some instances, a flexible fluid reservoir facilitates transporting the fluid from the fluid reservoir through the conduit, while maintaining the sterility of the sample fluid. For example, during use, the pliant sample container is placed in the pressure chamber and pressure is applied to the fluid reservoir to transport the fluid from the fluid reservoir through the conduit. In certain cases, pressure is applied to the fluid reservoir by increasing the pressure in the pressure chamber, for instance by pressurizing the pressure chamber with a gas.

As indicated above, the fluid reservoir may be made of a flexible material. The fluid reservoir may be made of a thin material that facilitates the flexibility of the fluid reservoir. In certain embodiments, the fluid reservoir is made of a thin material but still has sufficient strength to operate in the elevated pressures in the pressure chamber while maintaining its structural integrity. For instance, the fluid reservoir may be configured to operate in pressures of 25 psi or more, such as 50 psi or more, or 75 psi or more, including 100 psi or more, or 125 psi or more, for example 150 psi or more, while maintaining its structural integrity, such that the seal between the sample fluid and the surrounding environment is not significantly compromised. In certain embodiments, the fluid reservoir is made of a material with a thickness of 5 mm or less, or 3 mm or less, such as 2 mm or less, including 1 mm or less, or 0.5 mm or less, such as 0.4 mm or less, or, 0.3 mm or less, or 0.2 mm or less, or 0.1 mm or less.

The fluid reservoir may be made of any material that is compatible with the assay conditions, e.g., the sample solution buffer, pressure, temperature, etc. In some cases, the fluid reservoir may be made of a material that is inert and does not substantially react with the sample fluid or components in the sample fluid. For example, the fluid reservoir may include materials that are substantially non-reactive to the sample, the components in the sample, the buffer, and the like. In some embodiments, the fluid reservoir is made of a polymer, such as, but not limited to, polyvinyl chloride (PVC), ethyl vinyl acetate (EVA), polyethylene, polypropylene, combinations thereof, and the like.

In certain embodiments, the fluid reservoir includes one chamber that includes the fluid. In other cases, the fluid reservoir includes two or more chambers. The two or more chambers may contain the same or different fluids. For example, a first fluid reservoir chamber may contain a first fluid and a second fluid reservoir chamber may contain a second fluid. A fluid reservoir comprising two or more chambers may facilitate the analysis of two or more sample fluids, where the first sample fluid is contained in the first fluid reservoir chamber and the second sample fluid is contained in the second fluid reservoir chamber. The two or more chambers may be configured to be in fluid communication with a single conduit or with two or more conduits, as desired. For instance, the two or more chambers may be in fluid communication with one conduit. The lumens of the two or more chambers may be joined together at a Y-connector, a valve (e.g., a pinch valve), or the like.

Conduit

Aspects of the pliant sample container further include a conduit. In certain embodiments, the conduit is fluidically coupled to the fluid reservoir and configured to direct a flow of the fluid through a magnetic separation device. For example, the conduit may be in fluid communication with and positioned downstream from the fluid reservoir. The conduit may be configured to direct a flow of the sample fluid through the magnetic separation device. As such, the conduit may be configured to carry the flow of the sample (e.g., a sample solution). In certain embodiments, the conduit is enclosed, such that the conduit is defined by outer walls that surround a central flow path. The central flow path may be aligned with a longitudinal axis of the conduit. The central flow path may have any convenient shape, such as, but not limited to, a flow path with a cross-sectional profile of a circle, an ellipse, a square, a rectangle, a pentagon, a hexagon, an irregular cross-sectional profile, combinations thereof, and the like. In certain instances, the central flow path of the conduit has a cross-sectional profile of a circle. During use, the conduit may also be configured to retain the magnetically labeled components in the sample.

In certain embodiments, the conduit may be configured to direct a flow of the sample through the magnetic separation device such that the sample flow is proximal to the magnetic field source. Minimizing the distance between the magnetic field source and the sample, and thereby minimizing the distance between the magnetic field source and the magnetically labeled components in the sample may facilitate the retention of the magnetically labeled components in the device. In some cases, the conduit is configured to direct the flow of the sample through the device to maximize the length of the flow path that is proximal to the magnetic field source. For example, the conduit may be configured to direct the flow of the sample through the device such that the sample flow is substantially parallel to the longitudinal axis of the magnetic field source.

In some instances, at least a portion of the conduit is positioned between the magnetic field sources, such as between the first magnetic field source and the second magnetic field source. In certain cases, the magnetic field sources may be associated with magnetic field guides as described above, and at least a portion of the conduit may be positioned between the magnetic field guides, such as between the first magnetic field guide and the second magnetic field guide. The conduit may be positioned between the first and second magnetic field guides such that a longitudinal axis of the conduit is substantially parallel to a longitudinal axis of the first magnetic field guide and a longitudinal axis of the second magnetic field guide. For example, the conduit may be positioned between the first and second magnetic field guides such that the longitudinal axis of the conduit is substantially parallel to the apex edges of each of the first and second magnetic field guides. In some cases, positioning the conduit substantially parallel to the apex edges of the magnetic field guides maximizes the length of conduit, and thus the flow of sample fluid, that is between the magnetic field guides. In certain instances, positioning the conduit substantially parallel to the apex edges of the magnetic field guides maximizes the amount of time the flow of the sample is between the magnetic field guides. This alignment between the conduit and the magnetic field guides may facilitate retaining the magnetically labeled components in the conduit.

In some instances, the conduit is configured to have a narrower cross-sectional area in the portion of the conduit positioned between the magnetic field guides. For example, the cross-sectional area of the conduit upstream from the portion of the conduit positioned between the magnetic field guides may be greater than the cross-sectional area of the portion of the conduit positioned between the magnetic field guides. Similarly, the cross-sectional area of the conduit downstream from the portion of the conduit positioned between the magnetic field guides may be greater than the cross-sectional area of the portion of the conduit positioned between the magnetic field guides. Thus, in some cases, a portion of the conduit positioned between the first and second magnetic field guides has a cross-sectional area less than the cross-sectional area of a portion of the conduit upstream or downstream from the portion of the conduit positioned between the first and second magnetic field guides.

In certain embodiments, the conduit may be positioned in the magnetic separation device manually. For example, the conduit may be manually aligned between the magnetic field guides, and may be manually removed from between the magnetic field guides. The conduit may be configured to have one or more alignment guides on the exterior of the conduit, such as, but not limited to, a notch, a tab, a groove, a guide post, etc., which may facilitate positioning of the conduit in the magnetic separation device. In some embodiments, the subsystem may be configured to automatically position the conduit in the magnetic separation device. For example, the subsystem may be configured to automatically position the conduit in the magnetic separation device, such that the pressure chamber may be sealed and not reopened to position the conduit in the magnetic separation device. The conduit may include one or more markings or alignment guides as described above that the subsystem may use to position the conduit in the magnetic separation device.

In some instances, the conduit is configured to be positionable away from the magnetic separation device. For example, the conduit may be configured to be positionable away from the magnetic field produced by the magnetic separation device, e.g., positionable away from the magnetic field sources and the magnetic field guides of the magnetic separation device. Positioning the conduit away from the magnetic field may facilitate the recovery of magnetically labeled components that were retained in the conduit during an assay. In certain cases, the device may be configured to automatically position the conduit away from the magnetic separation device. In these instances, subsystems configured to automatically position the conduit away from the magnetic separation device may facilitate recovery of retained magnetically labeled components from the conduit without the need to open the pressure chamber and reposition the conduit away from the magnetic separation device manually.

In some instances, the conduit is configured to be removably coupled to the fluid reservoir. The conduit may include a connector at an end proximal to the fluid reservoir, and the fluid reservoir may include a connector configured to mate with the connector on the conduit. In certain instances, the connector on the conduit and the connector on the fluid reservoir are configured to disconnect from each other such that the conduit is removably coupled to the fluid reservoir. In some cases, the connector on the conduit and the connector on the fluid reservoir are configured to mate together and form a seal that maintains the sterility of the fluid in the fluid reservoir and the conduit. For example, the connector on the conduit and the connector on the fluid reservoir are configured to mate together and form a seal that does not allow fluid in the conduit and/or fluid reservoir to contact the surrounding environment. Various types of connectors may be used, such as, but not limited to, Luer connectors, spike connectors, and the like.

In certain cases, the conduit is configured to be reusable. A reusable conduit may be configured to be washed between assays, such as, but not limited to, configured to be washed by flowing a wash solution or buffer through the conduit between assays. In some cases, the conduit is configured to be removed from the device, washed and then reinserted into the device for a subsequent assay. In certain embodiments, the conduit is configured to be disposable. By disposable is meant that the conduit may be used once or several times (e.g., 20 times or less, 15 times or less, 10 times or less, or 5 times or less) and then discarded and replaced by a new conduit.

For example, the conduit may be configured to be a single-use conduit, where the conduit is configured to be used for a single assay, and then removed and discarded. A new conduit may be used in a subsequent assay.

In certain embodiments, the conduit may have a height (e.g., for conduits that do not have a round cross-sectional profile) or an inside diameter (e.g., for conduits that have a round cross-sectional profile) of 5 cm or less, such as 2 cm or less, including 1 cm or less, or 7 mm or less, or 5 mm or less, or 3 mm or less, or 2 mm or less, or 1.5 mm or less, or 1 mm or less. The length of the conduit may range from 1 cm to 1000 cm, such as from 2 cm to 750 cm, including from 5 cm to 500 cm, or from 5 cm to 250 cm, or from 5 cm to 100 cm, such as from 5 cm to 50 cm, for example from 5 cm to 25 cm. In certain embodiments, the conduit has walls with a thickness of 5 mm or less, or 3 mm or less, such as 2 mm or less, including 1 mm or less, or 0.5 mm or less, 0.4 mm or less, or, 0.3 mm or less, or 0.2 mm or less, or 0.1 mm or less. In certain instances, a conduit with relatively thin walls facilitates separation of magnetically labeled components in the sample fluid by reducing the distance between the magnetically labeled components in the sample fluid and the magnetic field sources and/or magnetic field guides. For example, the conduit may have walls with a thickness of 1 mm or less.

In certain embodiments, the conduit is configured to be substantially free from magnetic gradient enhancing materials. For example, the conduit may be made of nonmagnetic and/or non-magnetizable materials. In some instances, the central flow path of the conduit is substantially free from magnetic gradient enhancing materials (excluding the magnetic labels). For instance, the central flow path of the conduit may be substantially free of any materials (e.g., matrix materials, magnetizable particles (e.g., magnetizable spheres/ellipsoids), magnetizable wires, magnetizable cylinders, and the like) other than the sample (e.g., including any buffer and magnetic labels, etc. used in the assay itself). In some instances, having a conduit with a central flow path substantially free of materials, such as magnetizable materials, facilitates the subsequent recovery of the separated magnetically labeled components. For example, the separated magnetically labeled components may be more easily flushed from the conduit when the conduit is substantially free of materials as compared to a conduit with materials, such as magnetizable materials, in the central flow path of the conduit. The separated magnetically labeled components may be more easily flushed from the conduit, for instance, due to the absence of restrictions to the fluid flow path in the conduit substantially free of materials and/or the absence of magnetizable materials in the flow path that may have remnant magnetizations that retain the magnetically labeled components in the conduit.

The conduit may be made of any material that is compatible with the assay conditions, e.g., the sample solution buffer, pressure, temperature, etc. For example, the conduit may include materials that are substantially non-reactive to the sample, the components in the sample, the buffer, and the like. The conduit may include a flexible material, such that the conduit is flexible. In certain instances, the conduit is configured to deform from its initial shape and/or stretch if the conduit is compressed between the apex edges of the magnetic field guides. The conduit may be configured to deform from its initial shape and/or stretch without breaking, splitting, tearing, etc., when the conduit is compressed between the magnetic field guides. In some instances, the conduit includes glass, or polymers, such as, but not limited to, silicone, polypropylene, polyethylene, polyether ether ketone (PEEK), polyvinyl chloride (PVC), ethyl vinyl acetate (EVA), and the like. In certain embodiments, the conduit includes a flexible material, such as a flexible polymer material (e.g., silicone, polyethylene, polypropylene, PEEK, etc.).

Alignment Guide

In certain embodiments, the pliant sample container includes an alignment guide attached to the conduit and configured to operatively couple the conduit with the magnetic separation device. The pliant sample container may include one or more alignment guides. For example, the conduit may be configured to have one or more alignment guides on the exterior of the conduit, such as, but not limited to, a notch, a tab, a ball, a groove, a channel, a guide post, etc., which may facilitate positioning of the conduit between the magnetic field guides. In some cases, the alignment guide is an elongated tab attached to the exterior of the conduit. The elongated tab may be attached to the exterior of the conduit such that the elongated tab is substantially parallel to a longitudinal axis of the conduit. In some instances, the alignment guide includes one or more balls attached to the exterior of the conduit. For instance, the alignment guide may include a ball attached at each end of the conduit. In certain instances, the alignment guide facilitates positioning the conduit in the magnetic separation device such that a longitudinal axis of the conduit is substantially parallel to a longitudinal axis of the magnetic separation device.

In some cases, the magnetic separation device includes a corresponding mating element for the alignment guide on the conduit. For example, the magnetic separation device may be configured to have one or more mating elements, such as, but not limited to, a notch, a tab, a groove, a channel, a guide post, etc., which correspond to the one or more alignment guides on the conduit. The one or more mating elements may facilitate positioning the conduit between the magnetic field guides of the magnetic separation device. In some cases, the mating element includes a notch configured to mate with the alignment guide. The notch may be configured to position the conduit in the magnetic separation device such that a longitudinal axis of the conduit is substantially parallel to a longitudinal axis of the magnetic separation device.

In certain embodiments, the conduit may be positioned between the magnetic field guides manually. For example, the conduit may be manually positioned in the magnetic separation device by aligning the alignment guide of the conduit with the corresponding mating element of the magnetic separation device. The conduit may be manually removed from the magnetic separation device. In some embodiments, the device may be configured to automatically position the conduit in the magnetic separation device. The conduit may include one or more markings or alignment guides as described above that the subsystem may use to automatically position the conduit in the magnetic separation device.

Fluid Transfer Tube

Aspects of the pliant sample container may further include a fluid transfer tube. The fluid transfer tube may be in fluid communication with and positioned downstream from the conduit. The fluid transfer tube may be configured to transport the fluid (e.g., the sample fluid) outside the pressure chamber. In certain instances, the fluid transfer tube facilitates transporting the fluid to additional downstream systems and/or devices for subsequent processing or analysis. For example, the fluid transfer tube may be configured to transport the magnetically labeled components that were separated from the sample fluid by the magnetic separation device to a device arranged downstream from the magnetic separation device, such as, but not limited to a concentration device (e.g., an acoustic concentrator), a flow cytometer, and the like.

In some instances, the fluid transfer tube is configured to be removably coupled to the conduit. For example, the fluid transfer tube may be configured to be removably couplable to a downstream end of the conduit. The fluid transfer tube may include a connector at an end proximal to the conduit, and the conduit may include a connector configured to mate with the connector on the fluid transfer tube. In certain instances, the connector on the fluid transfer tube and the connector on the conduit are configured to disconnect from each other such that the fluid transfer tube is removably coupled to the conduit. In some cases, the connector on the fluid transfer tube and the connector on the conduit are configured to mate together and form a seal that maintains the sterility of the fluid in the fluid transfer tube and the conduit. For example, the connector on the fluid transfer tube and the connector on the conduit may be configured to mate together and form a seal that does not allow fluid in the fluid transfer tube and/or conduit to contact the surrounding environment.

The fluid transfer tube may be made of any material that is compatible with the assay conditions, e.g., the sample solution buffer, pressure, temperature, etc. For example, the fluid transfer tube may include materials that are substantially non-reactive to the sample, the components in the sample, the buffer, and the like. The fluid transfer tube may include a flexible material, such that the fluid transfer tube is flexible. In certain instances, the fluid transfer tube is configured to deform from its initial shape and/or stretch if the fluid transfer tube is compressed. The fluid transfer tube may be configured to deform from its initial shape and/or stretch without breaking, splitting, tearing, etc., when the fluid transfer tube is compressed. In some instances, the fluid transfer tube includes polymers, such as, but not limited to, silicone, polypropylene, polyethylene, polyether ether ketone (PEEK), polyvinyl chloride (PVC), ethyl vinyl acetate (EVA), and the like. In certain embodiments, the fluid transfer tube includes a flexible material, such as a flexible polymer material (e.g., silicone, polyethylene, polypropylene, PEEK, etc.). In certain embodiments, the fluid transfer tube has an inner diameter of 5 cm or less, such as 2 cm or less, including 1 cm or less, or 7 mm or less, or 5 mm or less, or 3 mm or less, or 2 mm or less, or 1 mm or less.

As described above, subsystems of the present disclosure may include a valve, such as a check valve, configured to regulate the pressure inside the pressure chamber. In certain instances, at least a portion of the check valve is attached to the fluid transfer tube. For example, the check valve may be configured as a ball check valve. In some of these cases, the ball of the ball check valve may be attached to the fluid transfer tube. For instance, the ball of the ball check valve may include a central lumen with the fluid transfer tube running through the central lumen. In these instances, a first half of the ball is disposed on a first side of the fluid transfer tube and a second half of the ball is disposed on an opposing side of the fluid transfer tube. In some cases, the two halves of the ball include one or more connectors configured to attach the two halves of the ball to each other. For example, the connectors may include snaps, clips, notches, and the like. During use, the ball may be positioned in the check valve, sealing the pressure chamber and thus allowing pressure to build up inside the pressure chamber, while still permitting fluid to flow through the fluid transfer tube passing through the central lumen of the ball check valve.

Flow Cytometric Fluidic Subsystem Configurations

As described above, flow cytometric fluidic subsystems according to embodiments of the present disclosure include a magnetic separation device and a pliant sample container, where a portion of the pliant sample container is operatively coupled under pressure to the magnetic separation device. For example, the flow cytometric sample fluidic subsystem may be configured to maintain the portion of the pliant sample container operatively coupled to the magnetic separation device under pressure. In certain embodiments, the magnetic separation device is configured to operatively couple to a pliant sample container and produce a magnetic field inside the pressure chamber. For example, the magnetic separation device may be configured to produce a magnetic field proximal to the portion of the pliant sample container operatively coupled to the magnetic separation device. In certain cases, the flow cytometric sample fluidic subsystem includes one pressure chamber. The pliant sample container may be present inside of the pressure chamber. In some embodiments, the magnetic separation device is also present inside of the pressure chamber. For example, the magnetic separation device may be positioned on the bottom surface of the pressure chamber and configured to operatively couple to the pliant sample container, which is also housed inside the same pressure chamber.

An example of an embodiment of a flow cytometric sample fluidic subsystem with a magnetic separation device present inside of the pressure chamber is shown in the schematic illustration in FIG. 1. The pliant sample container 120 is depicted positioned inside a pressure chamber 101. The pliant sample container 120 includes a fluid reservoir 105 and conduit 106. The conduit 106 is fluidically coupled to the fluid reservoir 105. In addition, the pliant sample container 120 includes an alignment guide 107 attached to the conduit 106 and configured to operatively couple the conduit 106 with the magnetic separation device 104. For example, the alignment guide 107 is shown as an elongated tab configured to position the conduit 106 in the magnetic separation device 104 such that a longitudinal axis of the conduit 106 is substantially parallel to a longitudinal axis of the magnetic separation device 104. The pliant sample container 120 further includes one or more ports, such as port 111 and port 112. The ports may be configured as inlet or outlet ports. For example, port 111 may be configured as an inlet for the addition of sample, reagents, magnetic labels, etc., into the fluid reservoir 105. In some embodiments, the pliant sample container 120 also includes a fluid transfer tube 108. The fluid transfer tube 108 is coupled to the downstream end of the conduit 106 and may be removably coupled to the conduit 106. In addition, the fluid transfer tube 108 may include at least a portion of a check valve (e.g., ball 109) attached to the fluid transfer tube 108. As described above, the pressure chamber 101 includes an outlet 110 configured as a ball check valve. Ball 109 of the ball check valve is attached around fluid transfer tube 108. Ball 109 is shown positioned in outlet 110 to illustrate the ball check valve in a closed position. During use, the pressure chamber 101 is sealed by closing cover 103. Pressurized gas is added to the pressure chamber 101 through gas inlet 102, pressurizing the pressure chamber 101 and forcing sample fluid in the fluid reservoir 105 to flow through the conduit 106 positioned in the magnetic separation device 104 and out of the pressure chamber 101 through fluid transfer tube 108.

Figure 3:
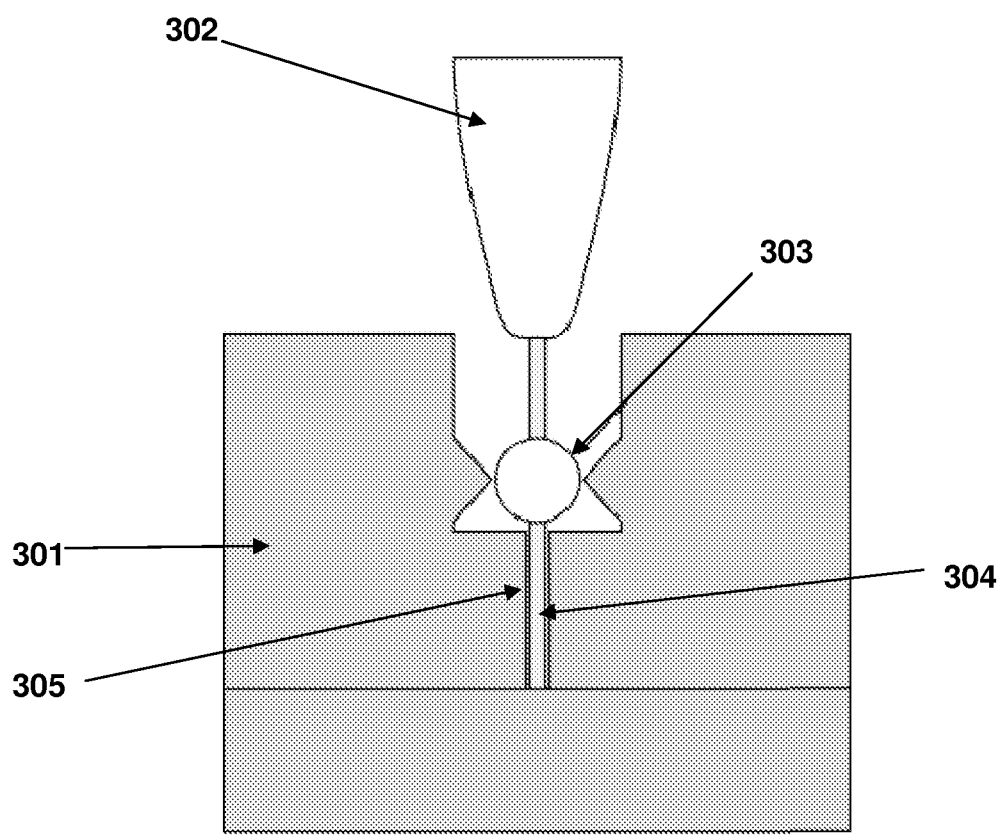
FIG. 3 shows a schematic cross-section of a pliant sample container positioned in a magnetic separation device, according to embodiments of the present disclosure.

FIG. 3 shows a schematic cross-section of a pliant sample container positioned in a magnetic separation device, according to embodiments of the present disclosure. Fluid reservoir 302 is in fluid communication with conduit 303, which is positioned in magnetic separation device 301. Alignment guide 304 is attached to the conduit 303 and facilitates positioning the conduit 303 in the magnetic separation device 301 such that a longitudinal axis of the conduit 303 is substantially parallel to a longitudinal axis of the magnetic separation device 301. The alignment guide 304 is a tab that fits into notch 305 in the magnetic separation device 301. The notch 305 is configured to mate with the alignment guide 304 and position the conduit 303 in the magnetic separation device 301 such that a longitudinal axis of the conduit 303 is substantially parallel to a longitudinal axis of the magnetic separation device 301.

Figure 4:
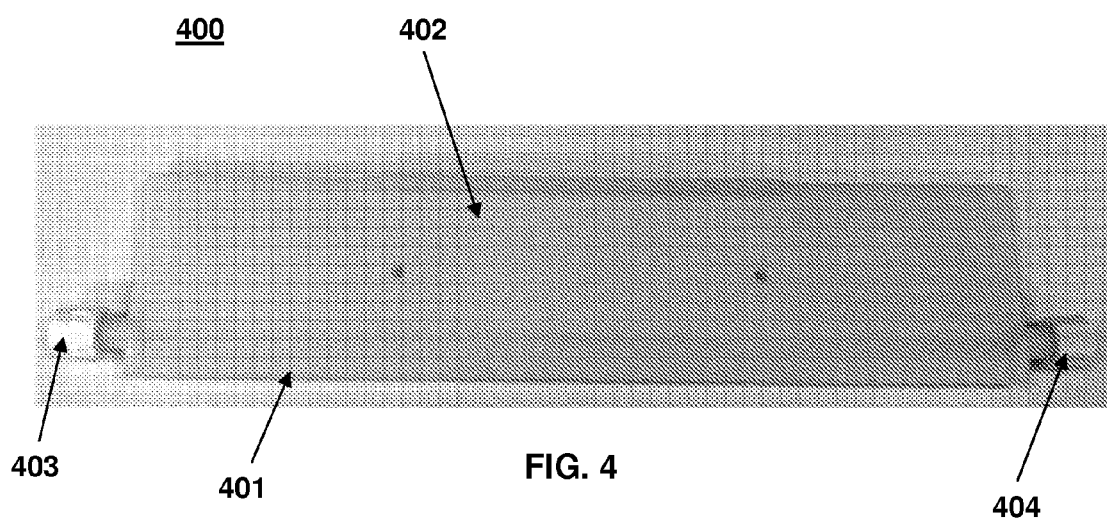
FIG. 4 is a photograph of a conduit, according to embodiments of the present disclosure.

FIG. 4 is a photograph of a conduit according to embodiments of the present disclosure. The conduit 400 includes a flow path 401 that carries the flow of the sample fluid through the magnetic separation device. The conduit 400 also includes an alignment guide 402 configured to position the conduit in the magnetic separation device as described above. Conduit 400 also includes two ports 403 and 404 which may be connected to a fluid reservoir or a fluid transfer tube as desired.

Figure 5A:
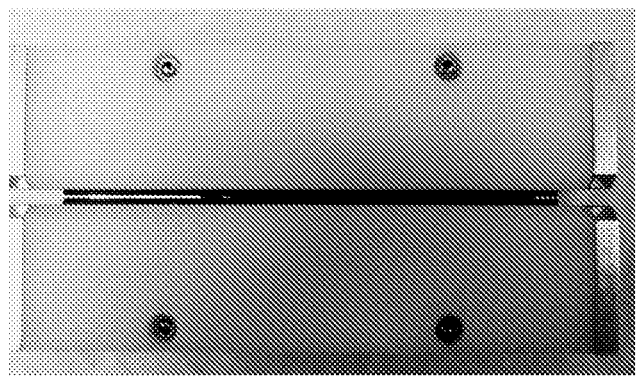
FIG. 5(a) is a photograph of a top view of a magnetic separation device.
Figure 5B:
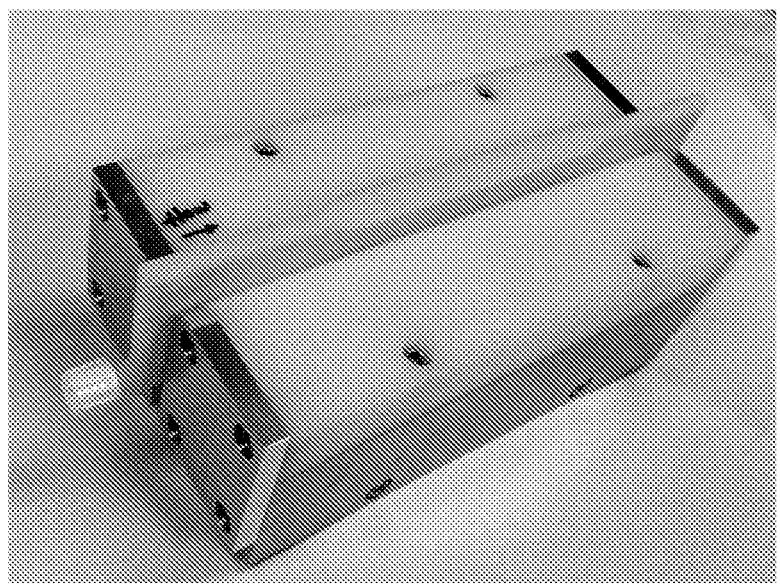
FIG. 5(b) is a photograph of a perspective view of a magnetic separation device with a conduit positioned in the magnetic separation device, according to embodiments of the present disclosure.

FIG. 5(a) is a photograph of a top view of a magnetic separation device, according to embodiments of the present disclosure. FIG. 5(b) is a photograph of a conduit positioned between the magnetic field guides in a magnetic separation device, according to embodiments of the present disclosure. The conduit is positioned within the gap between the opposing apex edges of the magnetic field guides. A liquid sample with magnetically labeled biological or chemical components flows within the conduit and along the tapered apex edges of the magnetic field guides. The magnetic field and magnetic field gradient produced by the magnetic field sources attracts the magnetic labels and magnetically labeled components from the flowing sample. The magnetic labels and magnetically labeled components are then pulled to and are retained at the inner surface of the conduit proximal to the apex edges of the magnetic field guides. Thus, magnetic labels and magnetically labeled components are separated from the flowing solution and retained within the conduit. After the solution sample is flowed through the conduit and a plurality of magnetic labels and magnetically labeled components are separated from the flowing solution, conduit is then removed from the gap between the magnetic field guides and the magnetic field within the conduit becomes approximately zero. By flushing the retained magnetic labels and magnetically labeled components within the conduit from the conduit with a buffer solution, the magnetic labels and magnetically labeled components can then be recovered from the conduit.

As described above, embodiments of the flow cytometric sample fluidic subsystem may include one pressure chamber. In certain cases, the magnetic separation device is positioned outside of the pressure chamber in an operative relationship with the pressure chamber. The magnetic separation device may be configured to produce a magnetic field inside the pressure chamber. For example, the magnetic separation device may be positioned such that at least a portion of the magnetic field sources are positioned outside of the pressure chamber. In some cases, the magnetic separation device includes a channel between the magnetic field guides. In certain embodiments, although at least a portion of the magnetic field source is positioned outside of the pressure chamber, the channel is open to the interior of the pressure chamber. In certain instances, the channel is configured to mate with and position the conduit of the sample container between the magnetic field guides. In some cases, the magnetic separation device is attached to the pressure chamber, such that the magnetic field sources are positioned outside of the pressure chamber while the channel between the magnetic field guides is open to the interior of the pressure chamber. In these embodiments, the mating surfaces between the pressure chamber and the magnetic separation device may be sealed together or permanently attached to each other, such that the pressure chamber is pressurizable as described according to embodiments of the present disclosure herein.

In other embodiments, a wall of the pressure chamber, such as the bottom or side wall of the pressure chamber, is configured to mate with the channel of the magnetic separation device. For example, the wall of the pressure chamber may be configured in a shape complimentary to the shape of the channel of the magnetic separation device, such that a portion of the wall of the pressure chamber fits within the channel of the magnetic separation device and is configured to position the conduit between the magnetic field guides of the magnetic separation device. In some instances, the magnetic separation device is not exposed to the interior of the pressure chamber, but is still configured to produce a magnetic field inside the pressure chamber of sufficient strength to separate magnetically labeled sample components from non-magnetically labeled components as described herein.

Figure 6:
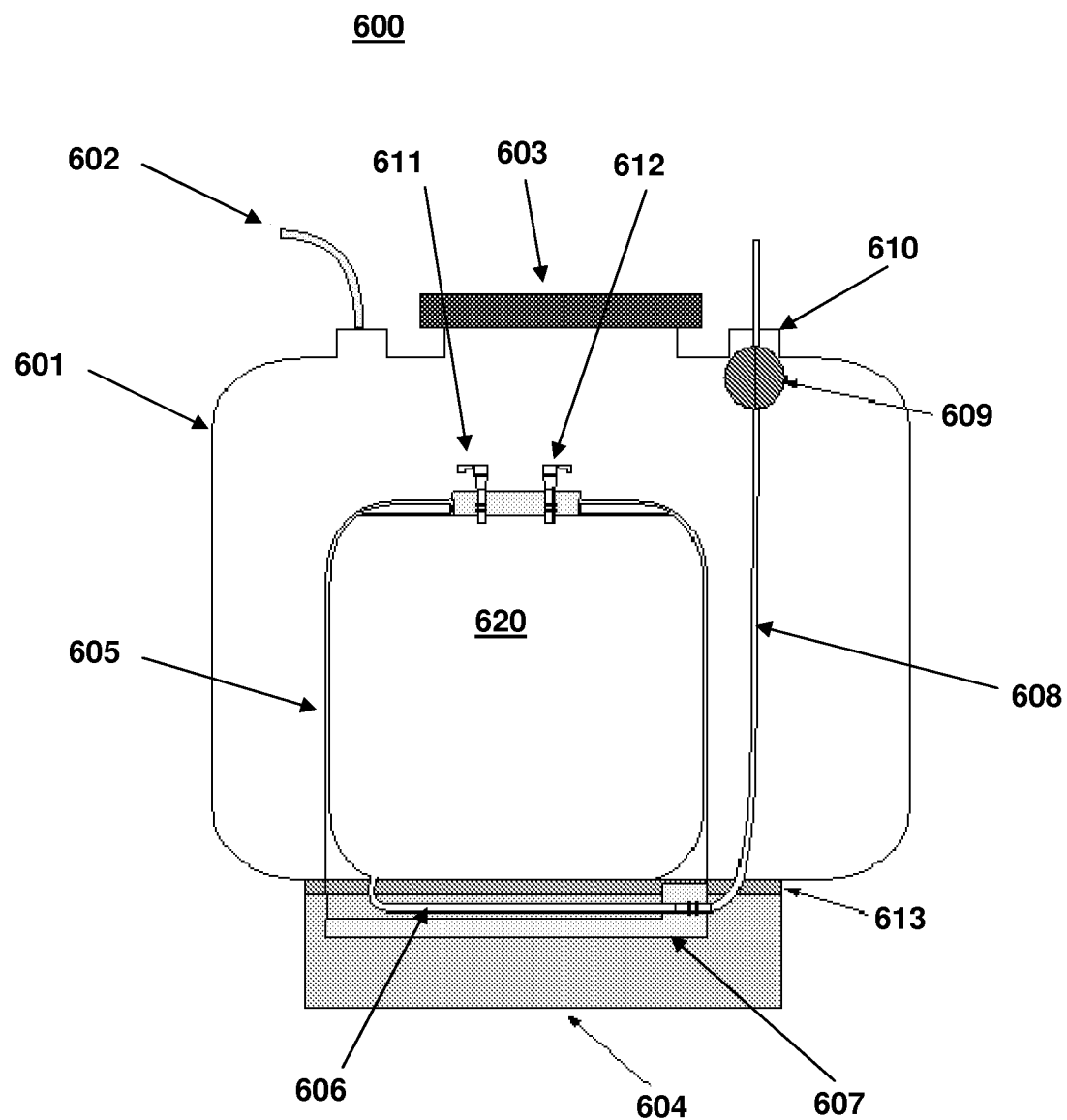
FIG. 6 shows a schematic of a system that includes a pressure chamber and a magnetic separation device configured to produce a magnetic field inside of the pressure chamber, according to embodiments of the present disclosure.

FIG. 6 shows an embodiment of a flow cytometric sample fluidic subsystem 600 with a magnetic separation device positioned outside of the pressure chamber. The pressure chamber 601 includes a gas inlet 602 for pressurizing the pressure chamber 601 with a pressurized gas. The pressure chamber 601 also includes a cover 603 through which the pliant sample container 620 may be inserted and withdrawn from the pressure chamber 601. The flow cytometric sample fluidic subsystem 600 also includes a magnetic separation device 604 positioned outside of and attached to the pressure chamber 601. The magnetic separation device 604 is configured to produce a magnetic field inside the pressure chamber 601. The magnetic separation device 604 includes a channel between the magnetic field guides, which is open to the interior of the pressure chamber 601, where the channel is configured to mate with an alignment guide 607 attached to the conduit 606 of the pliant sample container 620 and position the conduit 606 in the magnetic separation device 604. The magnetic separation device 604 may form a substantially air-tight seal to the pressure chamber 601. A gasket 613 may be provided between the pressure chamber 601 and the magnetic separation device 604 to facilitate forming an air-tight seal. The pliant sample container 620 also includes a fluid reservoir 605 and one or more inlet or outlet ports, such as port 611 and port 612, fluidically coupled to the fluid reservoir 605. In addition, the pliant sample container 620 includes a fluid transfer tube 608 coupled to the downstream end of the conduit 606. In addition, the fluid transfer tube 608 may include at least a portion of a check valve (e.g., ball 609) attached to the fluid transfer tube 608. As described above, the pressure chamber 601 includes an outlet 610 configured as a ball check valve. Ball 609 of the ball check valve is attached around fluid transfer tube 608. Ball 609 is shown positioned in outlet 610 to illustrate the ball check valve in a closed position.

Aspects of the flow cytometric sample fluidic subsystem include configurations that have more than one pressure chamber. For instance, embodiments of the flow cytometric sample fluidic subsystem may include two pressure chambers. In some instances, the flow cytometric sample fluidic subsystem includes a first pressure chamber housing a fluid reservoir of the pliant sample container (e.g., a sample container pressure chamber) and a second pressure chamber housing the portion of the pliant sample container operatively coupled to the magnetic separation device. The magnetic separation device may be configured to produce a magnetic field inside the second pressure chamber. For example, the magnetic separation device may be configured to produce a magnetic field proximal to the portion of the pliant sample container operatively coupled to the magnetic separation device positioned inside of the second pressure chamber. The first pressure chamber housing the pliant sample container may be configured as described above, with a gas inlet for receiving a pressurized gas and a cover that may be opened to access the inside of the first pressure chamber. In certain cases, the first pressure chamber is coupled to the second pressure chamber through a conduit. For example, the first and second pressure chambers may be coupled through a high pressure gas conduit. The high pressure gas conduit may be configured to allow gas to flow between the first and second pressure chambers, such that the pressures inside the first and second pressure chambers are substantially the same. For instance, if the first pressure chamber is pressurized with a high pressure gas, the conduit will allow the second pressure chamber to equalize pressures with the first pressure chamber, such that the pressures of the first and second pressure chambers are substantially the same. In certain instances, the flow cytometric sample fluidic subsystem also includes a high pressure fluid transfer conduit coupled at a first end to the first pressure chamber and coupled at a second end to the second pressure chamber. In some embodiments, the high pressure fluid transfer tube is configured to contain a fluid transfer tube of the pliant sample container. For instance, the high pressure fluid transfer tube may contain a portion of the fluid transfer tube that extends from the reservoir of the pliant sample container in the first pressure chamber to a conduit positioned in the magnetic separation device in the second pressure chamber. The high pressure fluid transfer tube may be made of any convenient material capable of retaining the elevated pressures within the pressure chamber without any significant structural changes, such as cracking, deformation from its original shape, etc. In some instances, the high pressure fluid transfer tube is made of a metal, such as stainless steel.

Figure 7:
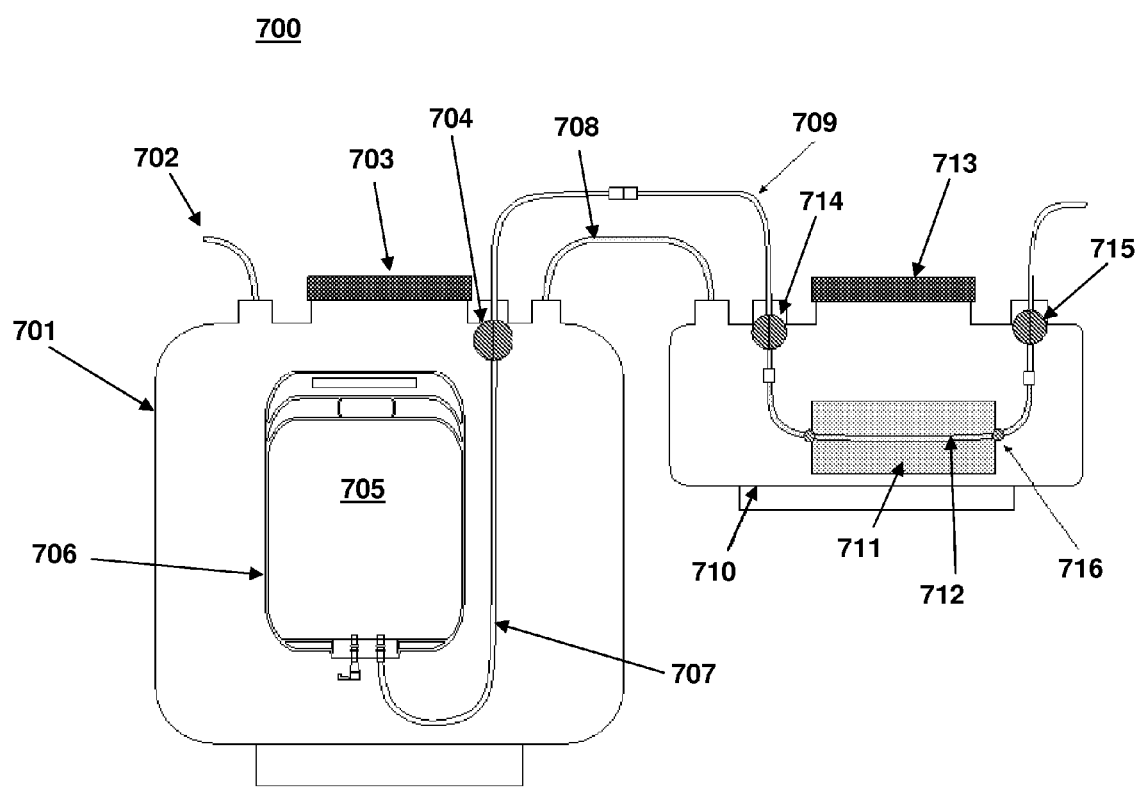
FIG. 7 shows a schematic of a system that includes a sample fluid pressure chamber and a magnetic separation device configured to produce a magnetic field inside of a second pressure chamber, according to embodiments of the present disclosure.

FIG. 7 shows an embodiment of a flow cytometric sample fluidic subsystem 700 that includes two pressure chambers: a first pressure chamber (e.g., the sample fluid pressure chamber) and second pressure chamber housing a magnetic separation device. The first pressure chamber 701 includes a gas inlet 702 for pressurizing the pressure chambers with a pressurized gas. The first pressure chamber 701 also includes a cover 703 through which a pliant sample container 705 may be inserted and withdrawn from the first pressure chamber 701. The flow cytometric sample fluidic subsystem 700 also includes a magnetic separation device 711 positioned in a second pressure chamber 710. The first pressure chamber 701 and the second pressure chamber 710 are connected through by a high pressure gas conduit 708 that allows gas to flow between the first pressure chamber 701 and the second pressure chamber 710, such that the gas pressure inside the first pressure chamber 701 and the second pressure chamber 710 are substantially the same. The pliant sample container 705 is housed in the first pressure chamber 701 and includes a fluid reservoir 706 and a fluid transfer tube 707. The fluid transfer tube 707 is configured to carry a sample fluid from the fluid reservoir 706 to the magnetic separation device 711 in the second pressure chamber 710. In addition, the fluid transfer tube 707 may include at least a portion of a check valve (e.g., ball 704) attached to the fluid transfer tube 707. In certain embodiments, the first pressure chamber 701 and the second pressure chamber 710 are also connected by a high pressure fluid conduit 709 configured to contain the fluid transfer tube 707.

The downstream end of the fluid transfer tube 707 may be connected to a conduit 712 positioned in the magnetic separation device 711 with the aid of one or more alignment guides 716. During use, pressurized air received through gas inlet 702 pressurizes the first pressure chamber 701 and the second pressure chamber 710 (via high pressure gas conduit 708) forcing the sample fluid from fluid reservoir 706 through the fluid transfer tube 707. The sample fluid then flows through the conduit 712, which is positioned in the magnetic separation device 711. The second pressure chamber may also include a cover 713, and one or more check valves, 714 and 715.

Although the magnetic separation device depicted in FIG. 7 is shown inside the second pressure chamber, other embodiments are possible. For example, the magnetic separation device may be positioned outside the second pressure chamber and configured to produce a magnetic field inside the pressure chamber, as described above (see e.g., FIG. 6).

In certain embodiments, the flow cytometric sample fluidic subsystem includes a wash fluid subsystem. The wash fluid subsystem may be configured to provide a flow of a wash fluid through the flow cytometric sample fluidic subsystem. In certain instances, the wash fluid subsystem is configured to provide a sterile wash fluid to the flow cytometric sample fluidic subsystem. Aspects of the sterile wash fluid subsystem are similar to the flow cytometric sample fluidic subsystem described herein. For example, the sterile wash fluid subsystem may include a wash fluid pressure chamber. A pliant wash fluid container that is configured to contain a volume of wash fluid may be provided in the wash fluid pressure chamber. Similar to the flow cytometric sample fluidic subsystem, the wash fluid pressure chamber may be configured to provide a flow of the wash fluid by increasing the pressure inside the wash fluid pressure chamber to force the wash fluid from the pliant wash fluid container into the flow cytometric sample fluidic subsystem.

In certain embodiments, the wash fluid subsystem is a separate subsystem from the flow cytometric sample fluidic subsystem and includes a separate wash fluid pressure chamber fluidically coupled to the flow cytometric sample fluidic subsystem. In other embodiments, the wash fluid subsystem is integrated into the flow cytometric sample fluidic subsystem. For example, the pliant wash fluid container may be provided in the same pressure chamber as the pliant sample fluid container. One or more fluid transfer tubes and one or more valves may be used to direct and control the flow of the sample fluid and the wash fluid through the flow cytometric sample fluidic subsystem. Any type of valve suitable for the assay conditions may be used, such as, but not limited to, a pinch valve, a stopcock, a needle valve, a ball valve, and the like. An example of an embodiment where the wash fluid subsystem is integrated into the flow cytometric sample fluidic subsystem is shown in FIG. 9(a).

Figure 9A:
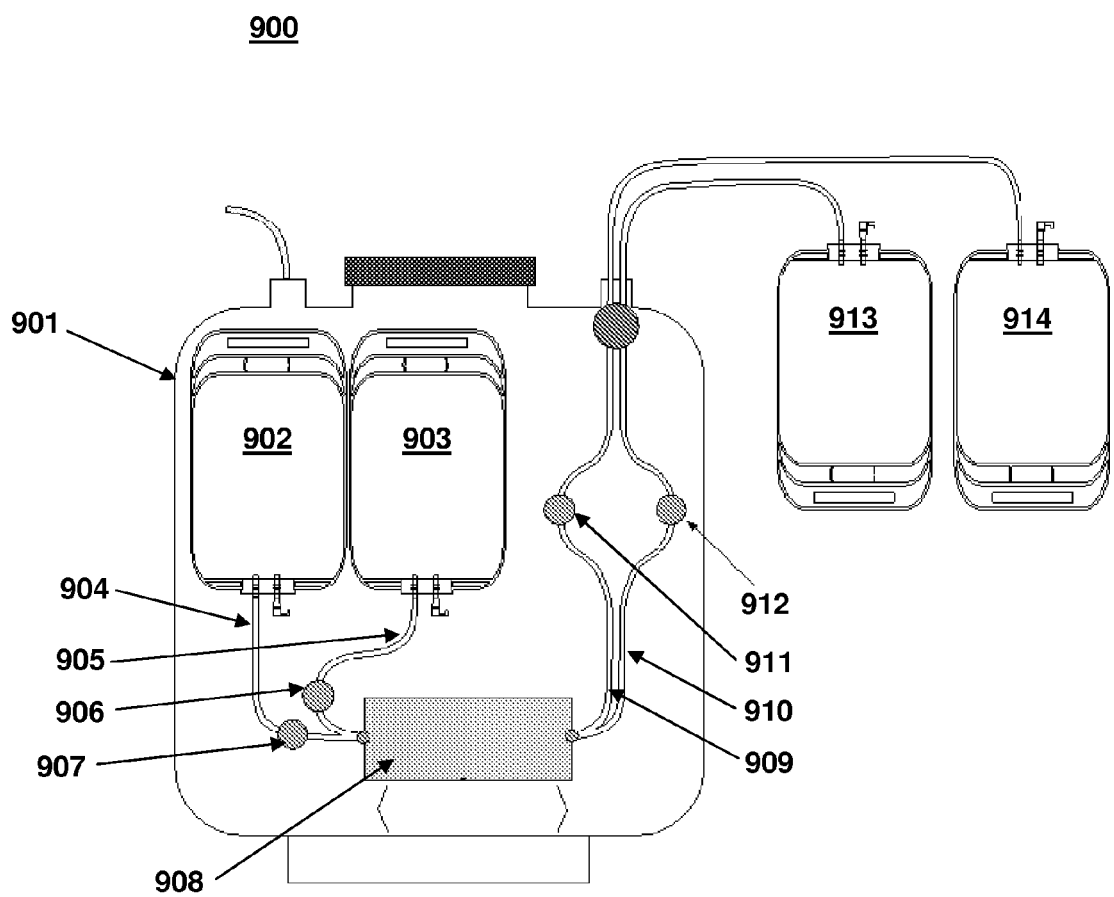
FIGS. 9(*a*)-9(*d*) show schematics of the sterile separation of magnetically labeled components from non-magnetically labeled components in a sample, according to embodiments of the present disclosure.
Figure 9B:
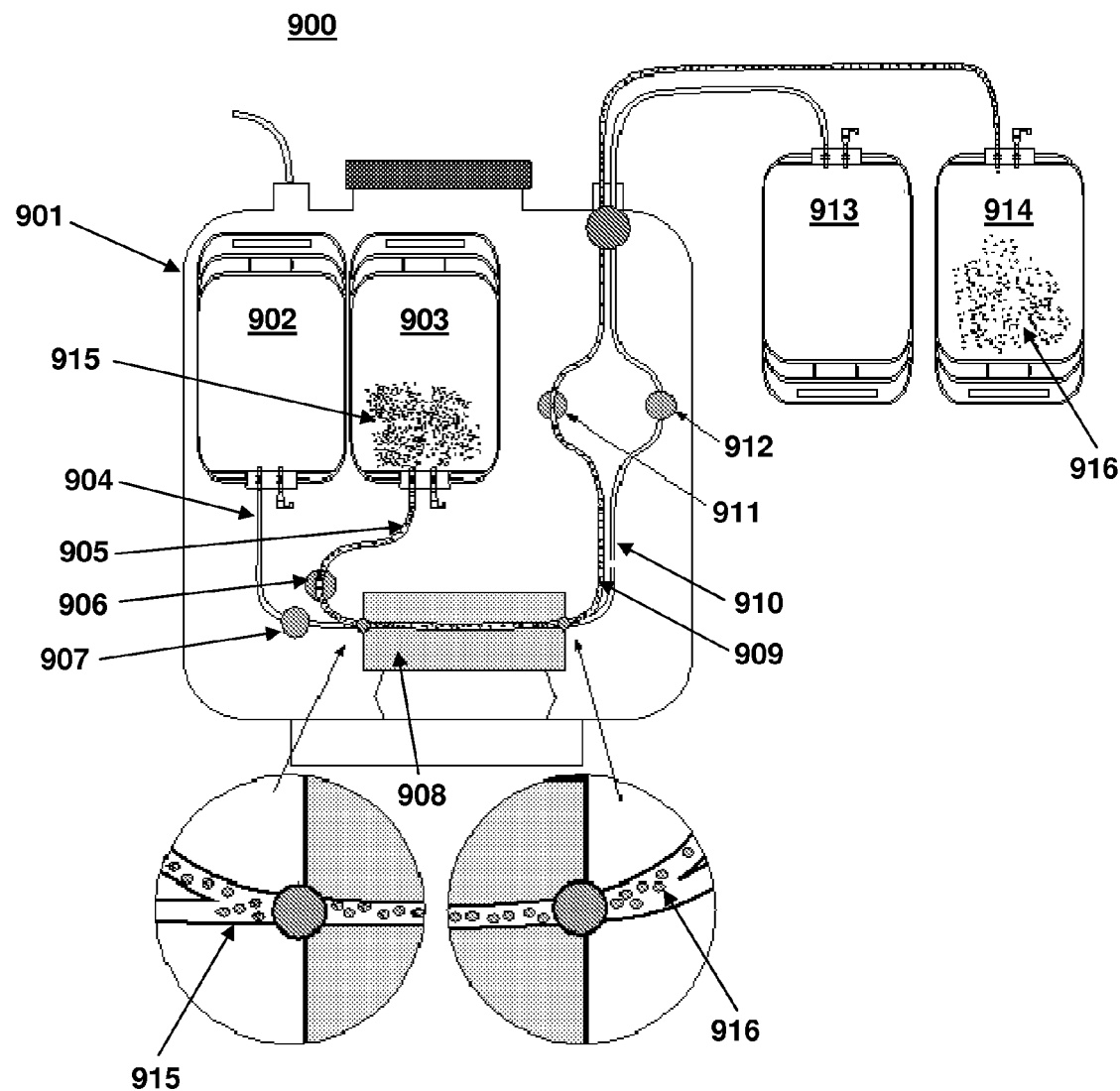
Figure 9C:
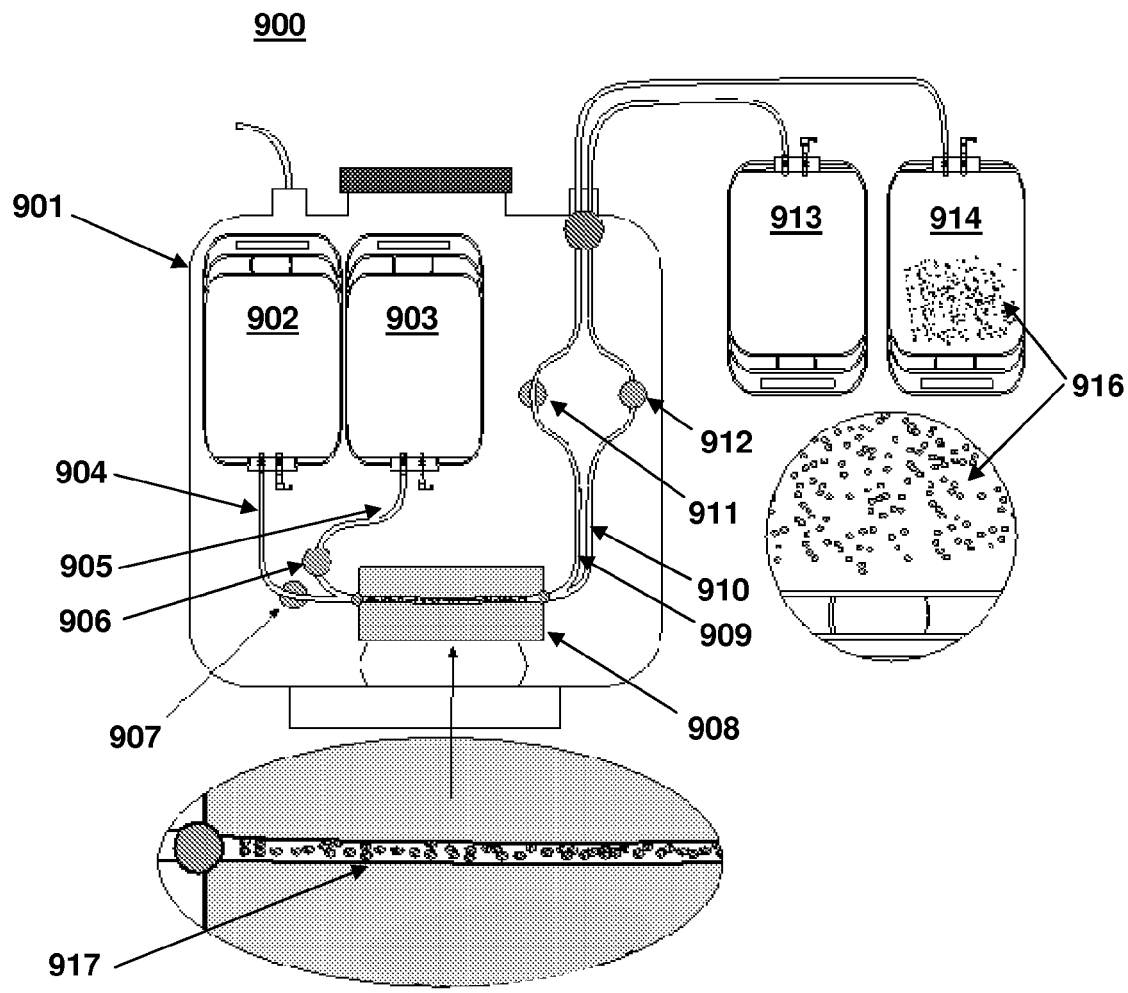
Figure 9D:
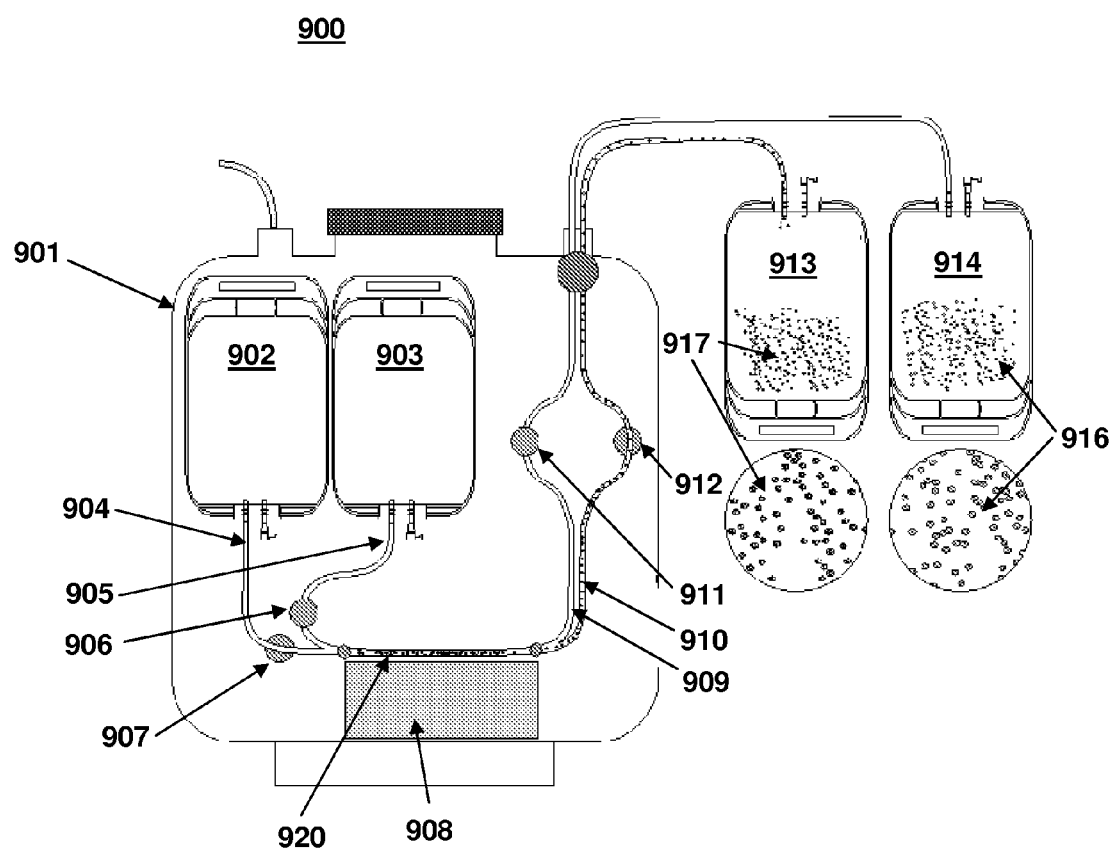

As shown in FIG. 9(a), the flow cytometric sample fluidic subsystem 900 includes a pressure chamber 901 that houses a pliant wash fluid container 902 and a pliant sample fluid container 903. The pliant wash fluid container 902 is fluidically coupled to a wash fluid transfer tube 904 configured to carry a wash fluid, and the pliant sample fluid container 903 is fluidically coupled to a sample fluid transfer tube 905 configured to carry a sample fluid. The wash fluid transfer tube 904 may have a wash fluid valve 907 configured to control the flow of the wash fluid to a magnetic separation device 908. The sample fluid transfer tube 905 may have a sample fluid valve 906 configured to control the flow of the sample fluid to the magnetic separation device 908. The wash fluid transfer tube 904 and the sample fluid transfer tube 905 may be fluidically coupled to each other, for example at a Y-junction, upstream from a conduit configured for magnetic separation in the magnetic separation device 908. Downstream from the conduit, the flow cytometric sample fluidic subsystem 900 may include an unlabeled component transfer tube 909 fluidically coupled to the downstream end of the conduit, and a labeled component transfer tube 910 fluidically coupled to the downstream end of the conduit. The unlabeled component transfer tube 909 and the labeled component transfer tube 910 may be fluidically coupled to each other, for example at a Y-junction, downstream from the conduit. The unlabeled component transfer tube 909 may have an unlabeled component fluid valve 911 configured to control the flow of the unlabeled component fluid to an unlabeled component collection container 914. The labeled component transfer tube 910 may have a labeled component fluid valve 912 configured to control the flow of the labeled component fluid to a labeled component collection container 913. Additional aspects regarding the operation of embodiments of the flow cytometric sample fluidic subsystem 900 depicted in FIG. 9(a) are shown in FIGS. 9(b)-9(d) and described in further detail below.

Flow Cytometric Systems

Aspects of the present disclosure also include flow cytometric systems. The flow cytometric systems include a flow cytometric sample fluidic subsystem, as described above. In addition, the flow cytometric systems include a flow cytometer fluidically coupled to the flow cytometric sample fluidic subsystem. For example, the flow cytometer may be in fluid communication with and positioned downstream from the flow cytometric sample fluidic subsystem. As reviewed above, the flow cytometric sample fluidic subsystem may be configured to separate magnetically labeled components in a sample fluid. The flow cytometric sample fluidic subsystem may be configured to provide the separated magnetically labeled components to one or more downstream devices, such as the flow cytometer. In some instances, the flow cytometer is configured to analyze the magnetically labeled components and determine information about the magnetically labeled components. For example, the flow cytometer may be configured to count the number of magnetically labeled components that were retained by the magnetic separation device. In some instances, the flow cytometer may be configured to sort the magnetically labeled components.

In certain embodiments, the systems include a sheath fluid subsystem. The sheath fluid subsystem may be configured to provide a flow of a sheath fluid to the flow cytometer. In certain instances, the sheath fluid subsystem is configured to provide a sterile sheath fluid to the flow cytometer. Aspects of the sterile sheath fluid subsystem are similar to the flow cytometric sample fluidic subsystem described herein. For example, the sterile sheath fluid subsystem may include a sheath fluid pressure chamber. A pliant sheath fluid container that is configured to contain a volume of sheath fluid may be provided in the pressure chamber. Similar to the flow cytometric sample fluidic subsystem, the sheath fluid pressure chamber may be configured to provide a flow of the sheath fluid by increasing the pressure inside the sheath fluid pressure chamber to force the sheath fluid from the pliant sheath fluid container into the flow cytometric system.

Additional aspects of the sheath fluid pressure chamber and pliant sheath fluid container are found in Jayasinghe, S. M. et al., *Cytometry Part B* (*Clinical Cytometry*), 70B:344-354 (2006).

Embodiments of systems of the present disclosure may also include a concentrator (e.g., a particle concentration device). The concentrator may be fluidically coupled to the flow cytometric sample fluidic subsystem. For example, the concentrator may be in fluid communication with and arranged downstream from the flow cytometric sample fluidic subsystem. In certain embodiments, the concentrator is arranged in series with the flow cytometric sample fluidic subsystem and the flow cytometer. For instance, the concentrator may be arranged between the flow cytometric sample fluidic subsystem and the flow cytometer. In some instances, the concentrator is configured to increase the concentration of magnetically labeled components in the eluent from the magnetic concentration device of the flow cytometric sample fluidic subsystem. The concentrator may be any type of concentrator, and in some embodiments is an acoustic concentrator.

Aspects of systems of the present disclosure may also include one or more additional particle analysis devices. The particle analysis device may be arranged downstream from the flow cytometric sample fluidic subsystem, and in certain instances may be arranged downstream from the concentrator or downstream from the flow cytometer. The particle analysis device may be configured to analyze the separated magnetically labeled components to determine one or more physical and/or chemical properties of the magnetically labeled components, such as, but not limited to, fluorescence, mass, charge, chemical composition, UV absorption, infrared absorption, light scattering, combinations thereof, and the like. In certain embodiments, the particle analysis device includes a mass spectrometer, an electrophoresis device, a high-performance liquid chromatography (HPLC) device, a UV spectrometer, an infrared spectrometer, and the like.

Systems of the present disclosure may further include other support devices and/or additional components that may facilitate the performance of the magnetic separation assay and/or any subsequent analysis of the separated magnetically labeled components (e.g., flow cytometry). For example, the system may further include a computer programmed to control the magnetic separation device, concentrator, flow cytometer, etc. The system may also include fluid handling components configured to provide a flow of the sample solution and/or buffer through the system (e.g., a pump, a vacuum source, a fluid reservoir, valves, inlets, outlets, etc.), and additional components associated with the magnetic separation device (e.g., motors configured to position the magnetic field sources and magnetic field guides), concentrator and flow cytometer.

The systems may generally include a processor configured to control the one or more magnetic separation devices. These two components may be integrated into the same article of manufacture as a single device, or distributed among two or more different devices (e.g., as a system) where the two or more different devices are in communication with each other, e.g., via a wired or wireless communication protocol.

Accordingly, aspects of the present disclosure further include systems, e.g., computer based systems, which are configured to separate magnetically labeled components in a sample as described above. A "computer-based system" refers to the hardware, software, and data storage devices used to analyze the information of the present invention. The minimum hardware of embodiments of the computer-based systems includes a central processing unit (CPU) (e.g., a processor), an input device, an output device, and data storage device. Any one of the currently available computer-based systems may be suitable for use in the embodiments disclosed herein. The data storage device may include any manufacture including a recording of the present information as described above, or a memory access means that can access such a manufacture. For example, embodiments of the subject systems may include the following components: (a) a communications module for facilitating information transfer between the system and one or more users, e.g., via a user computer or workstation; and (b) a processing module for performing one or more tasks involved in the analysis of the magnetically labeled components.

In addition, systems of the present disclosure may include a number of additional components, such as data output devices, e.g., monitors, printers, and/or speakers, data input devices, e.g., interface ports, a mouse, a keyboard, etc., fluid handling components, power sources, etc.

Figure 8:
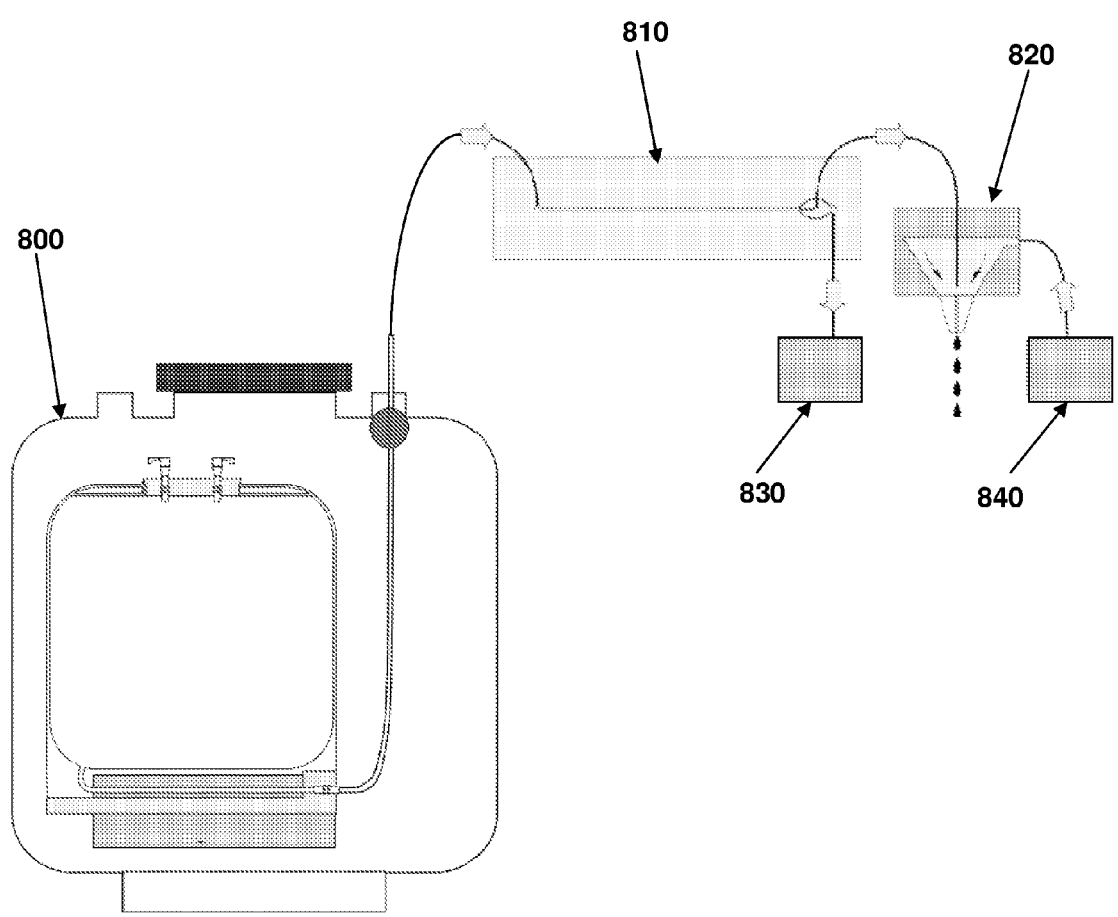
FIG. 8 shows a schematic of a system including a magnetic separation device in a pressure chamber, an acoustic concentrator and a flow cytometer, according to embodiments of the present disclosure.

FIG. 8 shows a schematic of a system including a magnetic separation device in a pressure chamber, an acoustic concentrator and a flow cytometer, according to embodiments of the present disclosure. As described above, the system includes a magnetic separation device in a pressure chamber 800 (see FIG. 1 for additional description). As shown in FIG. 8, the magnetic separation device in the pressure chamber 800, the acoustic concentrator 810 and the flow cytometer 820 are arranged in series, such that the fluid outlet of the magnetic separation device is in fluid communication with the fluid inlet of the acoustic concentrator 810, and the fluid outlet of the acoustic concentrator 810 is in fluid communication with the sample inlet of the flow cytometer 820. Also shown in FIG. 8 is a waste reservoir 830 for the acoustic concentrator 810 and a sheath fluid reservoir 840 for the flow cytometer 820. Arranging the magnetic separation device in the pressure chamber 800, the acoustic concentrator 810 and the flow cytometer 820 in series facilitates the separation, concentration and analysis of components of interest in a single integrated system.

Methods

Aspects of the present disclosure include methods for sterile separation of magnetically labeled sample components. As such, provided are methods of separating magnetically labeled components in a sample in a sterile manner. The magnetically labeled components may be separated from the other components of the sample, such as non-magnetically labeled components (e.g., components that are not associated with a magnetic label), while maintaining the sample fluid in a sterile environment.

In certain embodiments, the method includes operatively coupling a conduit of a pliant sample container to a magnetic separation device. In some cases, the pliant sample container includes a fluid reservoir fluidically coupled to the conduit and configured to contain a volume of fluid. In certain embodiments, the pliant sample container is placed into the pressure chamber through an opening in the pressure chamber. As described herein, the pressure chamber may be in an operative relationship with a magnetic separation device. In certain instances, the method includes positioning the conduit in the magnetic separation device. In some cases, the user positions the conduit in the device such that the conduit is aligned between the magnetic field guides of the device. Positioning the conduit may include aligning the conduit such that a longitudinal axis of the conduit is substantially parallel to a longitudinal axis of the magnetic separation device. For example, positioning the conduit may include aligning the conduit such that a longitudinal axis of the conduit is substantially parallel to a longitudinal axis of the magnetic field guides (e.g., the longitudinal axis of the first magnetic field guide and the longitudinal axis of the second magnetic field guide). In certain embodiments, the positioning is performed automatically by the flow cytometric sample fluidic subsystem. For example, the subsystem may be programmed to position the conduit in the magnetic separation device without the intervention of the user. In some cases, the device automatically aligns the conduit such that the longitudinal axis of the conduit is substantially parallel to the longitudinal axis of the magnetic field guides (e.g., the longitudinal axis of the first magnetic field guide and the longitudinal axis of the second magnetic field guide).

In certain embodiments, the method includes adding a sample that includes a target component of interest into the fluid reservoir. For example, in some cases, the pliant sample container is provided containing a fluid, such as, but not limited to, a buffer, a sheath fluid, and the like. The pliant sample container may be provided without any sample. In some cases, the sample is added to the pliant sample container prior to performing the assay. For instance, the sample may be added to the sample container immediately prior to performing a magnetic separation assay. As such, embodiments of the methods may include adding a sample that includes a target component to the fluid reservoir of the pliant sample container prior to applying pressure to the fluid reservoir to transport the fluid through the magnetic separation device. To facilitate maintaining the fluid in the fluid reservoir in a sterile condition, adding the sample to the fluid reservoir may include adding a sample fluid to the fluid reservoir without allowing the sample fluid or the fluid in the fluid reservoir to substantially contact the surrounding environment. For example, the sample fluid may be added to the fluid reservoir without significantly compromising the sealed configuration of the fluid reservoir. In some cases, a solution containing the sample is added into the fluid reservoir through a port (e.g., an inlet) in the fluid reservoir. For instance, the sample solution may be injected into the fluid reservoir prior to analyzing the sample fluid with the magnetic separation device.

Aspects of the methods disclosed herein may further include attaching a magnetic label to one or more target components in a sample prior to performing the magnetic separation assay (e.g., prior to applying the magnetic field to the sample). As such, the method may include magnetically labeling one or more components in a sample prior to performing the magnetic separation assay. The magnetic label may be stably associated with the component (or components) of interest through non-covalent or covalent interactions as described above. For example, the magnetic label may be associated with the component of interest through a binding interaction between a binding pair of molecules. To facilitate maintaining the sample fluid in a sterile condition, the method of attaching a magnetic label to the target component may include contacting the magnetic label to the target component without allowing the sample fluid to substantially contact the surrounding environment. For example, the magnetic label may be added to the fluid reservoir containing the sample fluid without significantly compromising the sealed configuration of the fluid reservoir. In some cases, a solution containing the magnetic label is added into the fluid reservoir through a port (e.g., an inlet) in the fluid reservoir. For instance, the magnetic label solution may be injected into the fluid reservoir prior to analyzing the sample fluid with the magnetic separation device.

After placing the pliant sample container in the pressure chamber, the method may include sealing the pressure chamber by closing the opening in the pressure chamber, for instance by closing a sealable cover over the opening.

Embodiments of the method further include applying pressure to the fluid reservoir to transport the sample fluid from the fluid reservoir through the magnetic separation device. In certain embodiments, applying pressure to the fluid reservoir includes pressurizing the pressure chamber with a gas. The pressure inside the pressure chamber causes fluid to flow from the fluid reservoir through the conduit, as pressure from the incoming pressurized gas squeezes the fluid reservoir, forcing fluid out from the fluid reservoir. In some cases, applying pressure to the fluid reservoir includes increasing the pressure in the pressure chamber to a pressure of 25 psi or more, such as 50 psi or more, or 75 psi or more, including 100 psi or more, or 125 psi or more, for example 150 psi or more. As described above, the fluid reservoir may be substantially sealed from contact with the surrounding environment. In these cases, applying pressure to the fluid reservoir, rather than to the sample fluid itself, facilitates maintaining the sterility of the sample fluid because the sample fluid does not contact the surrounding gas or environment.

Aspects of the method further include applying a magnetic field to the fluid. In some instances, the fluid includes a sample solution flowing through the conduit, thus the method includes applying a magnetic field to the sample flowing through the conduit. In certain instances, the method includes applying a magnetic field having a magnetic flux sufficient to separate magnetically labeled components from non-magnetically labeled components in the sample. The magnetic field may be applied continuously as the sample flows through the conduit, or may be applied discontinuously in a pulsed application. In certain embodiments, the magnetic field sources are permanent magnets as described above, and thus the magnetic field is applied continuously to the sample as the sample flows through the conduit.

In certain embodiments, the method includes positioning the conduit away from the magnetic field. The conduit may be positioned away from the magnetic field such that the applied external field on the conduit is substantially zero. Positioning the conduit away from the magnetic field may be achieved by removing the conduit from the magnetic separation device, such as by removing the conduit from the pressure chamber housing the magnetic separation device. For instance, the conduit may be removed from its position between the magnetic field guides and moved to a position away from the magnetic field sources and the magnetic field guides. Positioning the conduit away from the magnetic field may facilitate the subsequent recovery of any magnetically labeled components that were retained in the conduit during the assay. In certain instances, positioning the conduit away from the magnetic field may be performed manually by the user. In other embodiments, as discussed above, positioning the conduit away from the magnetic field may be performed automatically by the subsystem (e.g., without the intervention of the user).

In certain embodiments, after positioning the conduit away from the magnetic field, the magnetically labeled components retained in the conduit may be recovered by washing the magnetically labeled components from the conduit. For instance, the magnetically labeled components may be recovered by flowing a buffer or other compatible solution through the conduit to flush (e.g., wash) the magnetically labeled components from the conduit. Alternatively, the magnetically labeled components may be recovered from the conduit by centrifugation, application of a vacuum, pumping, combinations thereof, and the like.

Aspects of the methods disclosed herein may further include concentrating the recovered magnetically labeled components. After performing the magnetic separation assay as described herein, the magnetically labeled components that were retained in the conduit during the magnetic separation assay may be recovered from the conduit by washing the magnetically labeled components from the conduit as described above. In certain embodiments, it may be desirable to increase the concentration of the magnetically labeled components in the solution that is washed from the conduit. Thus, the method may include concentrating (e.g., increasing the concentration of) the magnetically labeled components in the solution that was washed from the conduit. Concentrating the magnetically labeled components may include passing the solution that was washed from the conduit that contains the magnetically labeled components through a concentration device. For example, the concentration device may include, but is not limited to, an acoustic concentrator. Further description of acoustic concentrators is found in U.S. Pat. No. 6,929,750, the disclosure of which is hereby incorporated by reference.

Aspects of methods of the present disclosure may further include analyzing the separated magnetically labeled components. In certain instances, the magnetically labeled components are analyzed subsequent to being separated from the non-magnetically labeled components in the sample, as described above. As such, the method may include analyzing the magnetically labeled components in the eluent from the magnetic separation device. In certain embodiments, the method includes analyzing the magnetically labeled components to determine information about the magnetically labeled components. For example, analyzing the magnetically labeled components may include counting the number of magnetically labeled components that were retained by the magnetic separation device. In some instances, the analyzing includes sorting the magnetically labeled components. For instance, the method may include counting and/or sorting the magnetically labeled components using a flow cytometry device. In certain cases, analyzing the magnetically labeled components includes determining one or more physical and/or chemical properties of the magnetically labeled components, such as, but not limited to, fluorescence, mass, charge, chemical composition, UV absorption, infrared absorption, light scattering, combinations thereof, and the like.

As described above, certain embodiments of the method include a washing step. For example, the magnetically labeled components that were retained in the conduit during the magnetic separation may be washed to elute the non-magnetically labeled components away from the retained magnetically labeled components. During subsequent recovery of the magnetically labeled components, the method may further include a subsequent wash step to elute the magnetically labeled components from the conduit as described above.

FIGS. 9(a)-9(d) show schematics of a flow cytometric sample fluidic subsystem 900 that includes an integrated wash fluid subsystem. Aspects of the flow cytometric sample fluidic subsystem are shown in FIG. 9(a) and described above. The flow cytometric sample fluidic subsystem 900 includes a pressure chamber 901 that houses a pliant wash fluid container 902 and a pliant sample fluid container 903. During use, the sample fluid valve 906 is opened and the pressure chamber is pressurized with a pressurized gas, which forces the sample fluid from the sample fluid container 903 through the sample fluid transfer tube 905 to the magnetic separation device 908. The wash fluid valve 907 is in a closed position, which prevents the wash fluid from flowing from the wash fluid container 902 through the wash fluid transfer tube 904. The sample fluid includes a mixture 915 of magnetically labeled and unlabeled sample components (see e.g., the left inset in FIG. 9(b)). As the sample flows through the magnetic separation device 908, the magnetically labeled components are retained in the magnetic separation device 908 and the unlabeled sample components 916 flow through the magnetic separation device 908 (see e.g., the right inset in FIG. 9(b)). The unlabeled sample components 916 that pass through the magnetic separation device 908 flow through the unlabeled component transfer tube 909 to the unlabeled component collection container 914. During this stage, the unlabeled component fluid valve 911 is in the open position allowing the unlabeled sample components 916 to flow to the unlabeled component collection container 914, while the labeled component fluid valve 912 on the labeled component transfer tube 910 is in the closed position, which prevents the flow of any fluids to the labeled component collection container 913.

During the next stage of the assay, as shown in FIG. 9(c), the retention of the magnetically labeled sample components 917 in the magnetic separation device 908 and the collection of the unlabeled sample components 916 in the unlabeled component collection container 914 is complete. The magnetically labeled sample components 917 retained in the magnetic separation device 908 may be washed with a wash fluid. During the washing step, the wash fluid valve 907 is opened and the pressurized gas in the pressure chamber 901 forces the wash fluid from the wash fluid container 902 through the wash fluid transfer tube 904 to the magnetic separation device 908. The sample fluid valve 906 is in a closed position, which prevents the sample fluid from flowing through the sample fluid transfer tube 905 and prevents the wash fluid from flowing back through the sample fluid transfer tube 905 to the sample fluid container 903. The wash fluid flows through the conduit in the magnetic separation device 908 washing residual unlabeled sample components away from the magnetically labeled sample components 917 retained in the magnetic separation device 908. The unlabeled component fluid valve 911 on the unlabeled component transfer tube 909 is in the open position allowing the wash fluid to flow to the unlabeled component collection container 914, while the labeled component fluid valve 912 on the labeled component transfer tube 910 is in the closed position, which prevents the flow of any fluids to the labeled component collection container 913.

After the washing step, the magnetically labeled sample components 917 retained in the magnetic separation device 908 may be collected, as shown in FIG. 9(d). During the collection step, the conduit 920 containing the magnetically labeled sample components 917 is positioned away from the magnetic field produced by the magnetic separation device 908, which facilitates the elution of the magnetically labeled sample components from the conduit 920 into the labeled component collection container 913. During the collection step, the wash fluid valve 907 is in the open position and the pressurized gas in the pressure chamber 901 forces the wash fluid from the wash fluid container 902 through the wash fluid transfer tube 904 and through the conduit 920. The sample fluid valve 906 is in a closed position, which prevents the sample fluid from flowing through the sample fluid transfer tube 905 and prevents the wash fluid from flowing back through the sample fluid transfer tube 905 to the sample fluid container 903. The wash fluid flows through the conduit 920 eluting the labeled sample components 917 out of the conduit 920. The labeled component fluid valve 912 on the labeled component transfer tube 910 is in the open position allowing the labeled sample components 917 to flow to the labeled component collection container 913. The unlabeled component fluid valve 911 on the unlabeled component transfer tube 909 is in the closed position, which prevents the labeled sample components 917 from flowing to the unlabeled component collection container 914.

Although the methods described above relate to embodiments that include one pressure chamber that houses the pliant sample container and the magnetic separation device, the methods disclosed herein may also be applied to embodiments that include a first pressure chamber housing a fluid reservoir of the pliant sample container and a second pressure chamber coupled to the first pressure chamber and housing the conduit of the pliant sample container operatively coupled to the magnetic separation device, as described above.

Figure 10:
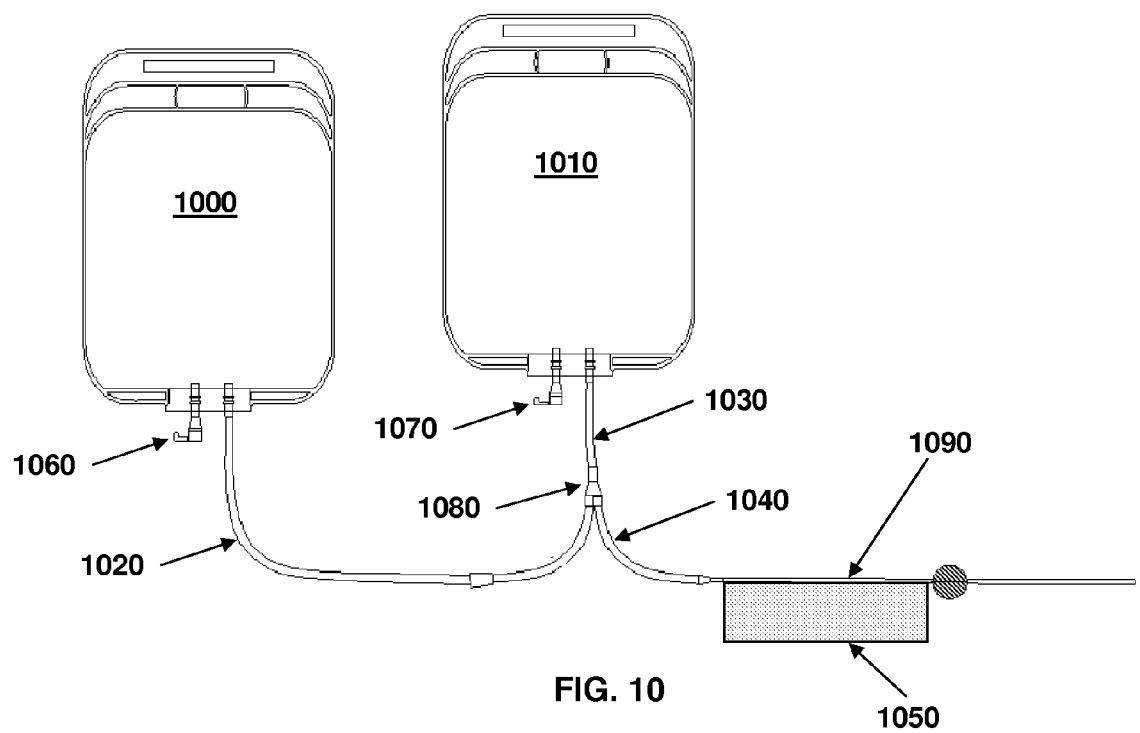
FIG. 10 shows a schematic of a wash buffer container fluidically coupled to the conduit of a pliant sample container fluidically, according to embodiments of the present disclosure.

As described above, the pliant wash fluid container may be in fluid communication with the pliant sample container. Embodiments include a configuration where the wash fluid transfer tube and the sample fluid transfer tube are fluidically coupled to each other, for example at a Y-junction, upstream from the magnetic separation conduit. For example, FIG. 10 shows an embodiment where the wash fluid transfer tube 1020 of the wash fluid container 1000 is fluidically coupled to the sample fluid transfer tube 1030 of the pliant sample fluid container 1010. The wash fluid transfer tube 1020 is fluidically coupled to the sample fluid transfer tube 1030 at a Y-junction 1080, which also connects the wash fluid transfer tube 1020 and the sample fluid transfer tube 1030 to a downstream fluid transfer tube 1040 that directs fluids to the conduit 1090 in the magnetic separation device 1050. A wash fluid valve (not shown) may be provided on the wash fluid transfer tube 1020 and a sample fluid valve (not shown) may be provided on the sample fluid transfer tube 1030 to direct and control the flow of fluids through the system, as described above. The wash fluid container 1000 and the sample fluid container 1010 may have ports, 1060 and 1070, respectively, for the removal and/or addition of buffer, reagents, sample, etc.

Figure 11:
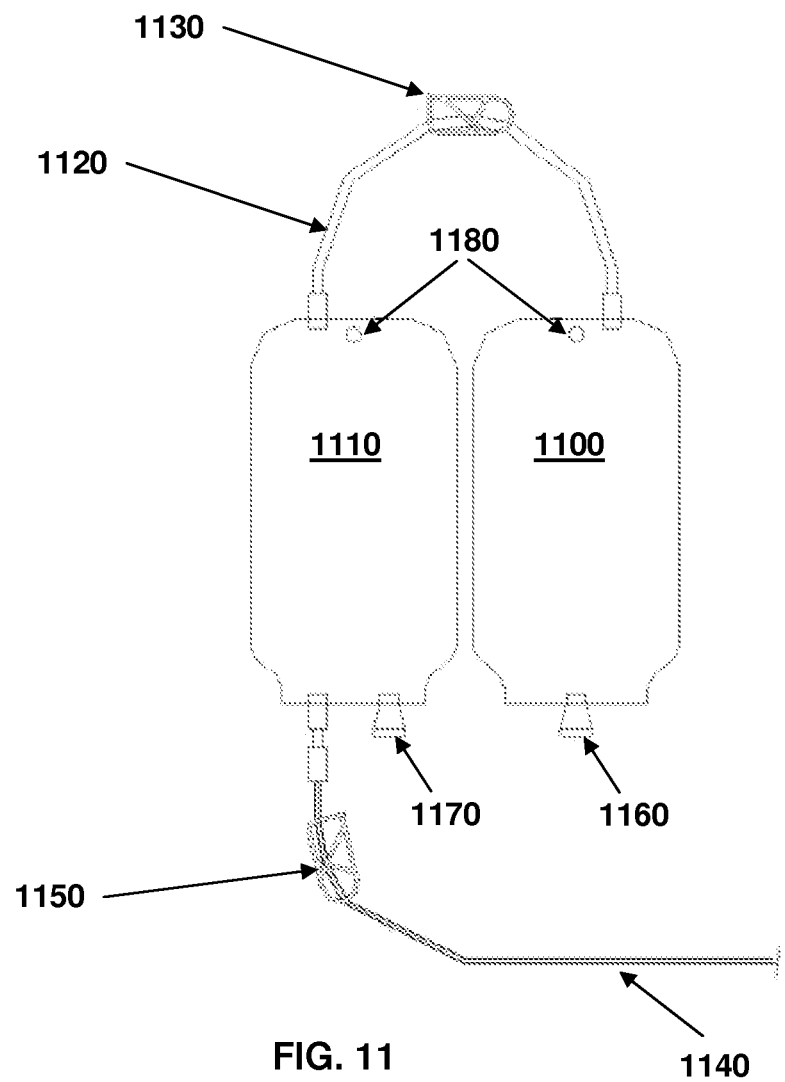
FIG. 11 shows a schematic of a wash buffer container fluidically coupled to the reservoir of the pliant sample container, according to embodiments of the present disclosure.

In other embodiments, for example as shown in FIG. 11, the wash fluid container may be fluidically coupled to the reservoir of the pliant sample container. FIG. 11 shows an embodiment where the wash fluid transfer tube 1120 of the wash fluid container 1100 is fluidically coupled to the reservoir of the sample fluid container 1110. The wash fluid transfer tube 1120 is connected to the top of the sample fluid container 1110, which in some cases, may facilitate washing of the sample fluid from the sample fluid container 1110 into the sample fluid transfer tube 1150. The sample fluid transfer tube 1140 directs the sample and/or wash fluids to the conduit in the magnetic separation device (not shown). A wash fluid valve, such as pinch valve 1130 is provided on the wash fluid transfer tube 1120 and a sample fluid valve, such as pinch valve 1150, is provided on the sample fluid transfer tube 1140 to control the flow of fluids through the system, as described above. The wash fluid container 1100 and the sample fluid container 1110 may have ports, 1160 and 1170, respectively, for the removal and/or addition of buffer, reagents, sample, etc. In addition, the wash fluid container 1100 and the sample fluid container 1110 may have attachment elements configured to attach the wash fluid container 1100 and the sample fluid container 1110 to the inside of the pressure chamber during use. Any convenient attachment element may be used, such as a hole, a slot, a hook, a tab, etc. For example, the wash fluid container 1100 and the sample fluid container 1110 may have holes 1180 for hanging the wash fluid container 1100 and the sample fluid container 1110 in the pressure chamber.

Utility

The subject devices, methods, systems and kits find use in a variety of different applications where it is desirable to separate magnetically labeled components from non-magnetically labeled components in a sample. The component of interest may be magnetically labeled and then separated from non-magnetically labeled components (e.g., by being retained in the conduit while non-magnetically labeled components flow through the conduit) by using the devices, methods, systems and kits described herein. In other embodiments, the component of interest is not magnetically labeled and other components that are not of interest in the sample are magnetically labeled. In these embodiments, the non-magnetically labeled components of interest are not retained by the device and flow through the conduit, where they may be collected and/or further analyzed. The magnetically labeled components that are not of interest are retained in the conduit and thus separated from the non-magnetically labeled components of interest.

Embodiments of the subject devices, methods, systems and kits find use in the sterile separation of magnetically labeled components from non-magnetically labeled components in a sample fluid. The subject devices, methods, systems and kits may be used to specifically label and separate components of interest in a sample fluid, while maintaining the sample fluid in a substantially sterile environment. The magnetically labeled components of interest that are retained in the conduit may be maintained in a substantially sterile environment and delivered to subsequent downstream analysis devices as such. In some cases, maintaining a sample in a sterile environment may facilitate subsequent processing or use of the components in the sample, for example in in vitro cell cultures, in vivo animal transplantations, collection of cellular proteins, and the like. In some cases, the sample fluid and/or magnetically labeled components of interest are maintained in a substantially sterile environment throughout the entire process, including for example, analysis and/or processing through one or more of a magnetic separation device, a concentration device, and a flow cytometer.

Kits

Also provided are kits for practicing one or more embodiments of the above-described methods and/or for use with embodiments of the devices and systems described above. The subject kits may include various components and reagents. Reagents and components of interest include those mentioned herein with respect to magnetic separation devices or components thereof, and include, but are not limited to, pliant sample containers, pliant sample containers pre-filled with a fluid, magnetic labels (e.g., magnetic nanoparticles), binding agents, buffers, sheath fluids, fluid flow conduits (e.g., disposable fluid flow conduits), fluid transfer tubes, syringes, etc. For example, embodiments of the kits may include a pliant sample container and a magnetic label specific for a target component of interest. The magnetic label may be provided in a separate container. For example, the magnetic label may be provided in a sterile solution in a sealed container separate from the pliant sample container.

As described above, the pliant sample container includes a fluid reservoir configured to contain a fluid, a conduit fluidically coupled to the fluid reservoir, and an alignment guide attached to the conduit and configured to operatively couple the conduit to the magnetic separation device. In some cases, the kit also includes a fluid transfer tube. The fluid transfer tube may be configured to be removably couplable to the conduit. In certain embodiments, the kits may further include at least a portion of a check valve attached to the fluid transfer tube. For example, the kits may include a ball of a ball check valve attached to the fluid transfer tube.

In some instances, the kits include at least reagents finding use in the methods (e.g., as described above); and a computer readable medium having a computer program stored thereon, wherein the computer program, when loaded into a computer, operates the computer to perform a magnetic separation assay as described herein; and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., CD, DVD, Blu-Ray, flash memory, etc., on which the information has been recorded. Yet another means that may be present is a website address which may be used via the Internet to access the information at a removed site. Any convenient means may be present in the kits.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A flow cytometric sample fluidic subsystem comprising:
   a sealed pressure chamber comprising an inlet operably coupled to a pressurized gas source;
   a magnetic separation device; and
   a pliant sample container made from a flexible material that has a Young's modulus of 1 GPa or less;
   wherein the pliant sample container and magnetic separation device are present inside of the sealed pressure chamber such that an elevated pressure may be maintained in the sealed pressure chamber that is sufficient to squeeze fluid out of the pliant container and a portion of the pliant sample container is operatively coupled to the magnetic separation device; and further wherein the flow cytometric sample fluidic subsystem comprises a fluid transfer tube configured to transport a fluid outside the sealed pressure chamber, wherein the fluid transfer tube is fluidically coupled to a flow cytometer.

2. The flow cytometric sample fluidic subsystem of claim 1, wherein the magnetic separation device comprises an alignment guide configured to mate with and position the portion of the pliant sample container in the magnetic separation device.

3. The flow cytometric sample fluidic subsystem of claim 1, further comprising a valve configured to regulate the pressure inside the sealed pressure chamber.

4. The flow cytometric sample fluidic subsystem of claim 3, wherein the valve is a check valve.

5. The flow cytometric sample fluidic subsystem of claim 1, wherein the pliant sample container comprises a sterile fluid.

6. The flow cytometric sample fluidic subsystem of claim 5, wherein the sealed pressure chamber comprises an internal pressure sufficient to squeeze sterile fluid out of the pliant container.

7. The flow cytometric sample fluidic subsystem of claim 1, wherein the magnetic separation device comprises a magnetic field guide disposed on a surface of a magnetic field source and configured to direct a magnetic field from the magnetic field source to a sample flow path.

8. The flow cytometric sample fluidic subsystem of claim 1, wherein the magnetic separation device comprises a magnetic field guide disposed on a surface of a magnetic field source and configured to direct a magnetic field from the magnetic field source to a sample flow path.

9. The flow cytometric sample fluidic subsystem of claim 1, wherein the elevated pressure is 25 psi or more.

* * * * *